United States Patent
Park et al.

(10) Patent No.: US 12,324,351 B2
(45) Date of Patent: *Jun. 3, 2025

(54) ORGANIC ELECTROLUMINESCENCE DEVICE AND COMPOUND FOR ORGANIC ELECTROLUMINESCENCE DEVICE

(71) Applicant: Samsung Display Co., LTD., Yongin-si (KR)

(72) Inventors: Hye Jeong Park, Hwaseong-si (KR); Daehyeon Kim, Hwaseong-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 48 days.

This patent is subject to a terminal disclaimer.

(21) Appl. No.: 18/495,915

(22) Filed: Oct. 27, 2023

(65) Prior Publication Data

US 2024/0074309 A1 Feb. 29, 2024

Related U.S. Application Data

(63) Continuation of application No. 17/072,654, filed on Oct. 16, 2020, now Pat. No. 11,849,635.

(30) Foreign Application Priority Data

Feb. 28, 2020 (KR) .................. 10-2020-0025076

(51) Int. Cl.
| | | |
|---|---|---|
| H10K 85/60 | (2023.01) | |
| C07D 401/14 | (2006.01) | |
| C07D 403/14 | (2006.01) | |
| C07D 471/04 | (2006.01) | |
| H10K 50/155 | (2023.01) | |
| H10K 50/16 | (2023.01) | |

(52) U.S. Cl.
CPC ......... *H10K 85/654* (2023.02); *C07D 401/14* (2013.01); *C07D 403/14* (2013.01); *C07D 471/04* (2013.01); *H10K 85/633* (2023.02); *H10K 85/6572* (2023.02); *H10K 85/6574* (2023.02); *H10K 50/155* (2023.02); *H10K 50/166* (2023.02)

(58) Field of Classification Search
None
See application file for complete search history.

(56) References Cited

U.S. PATENT DOCUMENTS

| | | |
|---|---|---|
| 7,273,663 B2 | 9/2007 | Liao et al. |
| 8,241,763 B2 | 8/2012 | Buesing et al. |
| 9,252,368 B2 | 2/2016 | Aihara et al. |
| 10,411,192 B2 | 9/2019 | Kato et al. |
| 11,588,111 B2 | 2/2023 | Sim et al. |
| 2010/0090588 A1 | 4/2010 | Yokoyama et al. |
| 2015/0364694 A1 | 12/2015 | Lee et al. |
| 2018/0006243 A1 | 1/2018 | Yoo et al. |

FOREIGN PATENT DOCUMENTS

| | | |
|---|---|---|
| CN | 107857759 | 3/2018 |
| KR | 10-1470340 | 12/2014 |
| KR | 10-2019-0015681 | 2/2019 |
| KR | 10-2022752 | 9/2019 |
| KR | 10-2003090 | 10/2019 |

*Primary Examiner* — Christopher M Rodd
(74) *Attorney, Agent, or Firm* — KILE PARK REED & HOUTTEMAN PLLC

(57) ABSTRACT

An organic electroluminescence device of an embodiment may include a first electrode, a hole transport region disposed on the first electrode, an emission layer disposed on the hole transport region, an electron transport region disposed on the emission layer, and a second electrode disposed on the electron transport region. The electron transport region may include a first compound represented by Formula 1, thereby improving the moving speed of electrons. Accordingly, the organic electroluminescence device of an embodiment may show decreased driving voltage and improved efficiency.

20 Claims, 4 Drawing Sheets

[Formula 1]

ORGANIC ELECTROLUMINESCENCE DEVICE AND COMPOUND FOR ORGANIC ELECTROLUMINESCENCE DEVICE

CROSS-REFERENCE TO RELATED APPLICATION(S)

This is a continuation application of U.S. patent application Ser. No. 17/072,654, filed Oct. 16, 2020, the disclosure of which is incorporated herein by reference in its entirety. U.S. patent application Ser. No. 17/072,654 claims priority to and benefits of Korean Patent Application No. 10-2020-0025076 under 35 U.S.C. § 119, filed Feb. 28, 2020, in the Korean Intellectual Property Office, the entire contents of which are incorporated herein by reference.

BACKGROUND

1. Technical Field

The disclosure relates to an organic electroluminescence device and a compound used therein.

2. Description of the Related Art

Recently, active development is being conducted for an organic electroluminescence display as an image display. In contrast to a liquid crystal display, the organic electroluminescence display includes an organic electroluminescence device and is a so-called self-luminescent display in which holes and electrons injected from a first electrode and a second electrode recombine in an emission layer, and a light-emitting material including an organic compound in the emission layer emits light to implement display.

In the application of an organic electroluminescence device to a display device, there is a continuous demand for the improvement of light emission efficiency, and for development of materials for an organic electroluminescence device that are capable of stably attaining such properties.

SUMMARY

The disclosure provides an organic electroluminescence device having a reduced driving voltage and high efficiency properties.

The disclosure also provides a compound for an organic electroluminescence device which may contribute to the improvement of the moving speed of electrons.

An embodiment of the inventive concept provides an organic electroluminescence device including a first electrode, a hole transport region disposed on the first electrode, an emission layer disposed on the hole transport region, an electron transport region disposed on the emission layer, and a second electrode disposed on the electron transport region. The electron transport region may include a first compound represented by Formula 1:

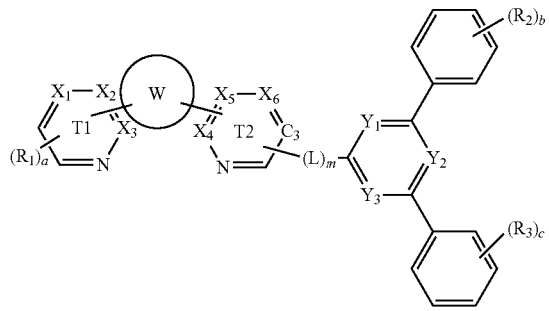

[Formula 1]

In Formula 1, $X_1$ to $X_6$ may each independently be N or $CR_4$, and W may be 0 or 1. If W is 0, then $X_3$ and $X_4$ may make a direct linkage. If W is 1, then W may be a substituted or unsubstituted hydrocarbon ring group of 4 to 60 ring-forming carbon atoms, or a substituted or unsubstituted heterocyclic group of 1 to 60 ring-forming carbon atoms, and W may be combined with ring T1 and ring T2 to form a polycyclic ring. In Formula 1, $C_3$ may be C or CH, m may be an integer from 0 to 3, and L may be a substituted or unsubstituted hydrocarbon ring group of 4 to 60 ring-forming carbon atoms, or a substituted or unsubstituted heterocyclic group of 1 to 60 ring-forming carbon atoms. If W, T1, and T2 are combined to form a phenanthroline group, then L may be bonded to $C_3$. In Formula 1, at least one of $Y_1$ to $Y_3$ may be N, the remainder of $Y_1$ to $Y_3$ may each independently be N or $CR_5$, a may be 1 or 2, b and c may each independently be an integer from 1 to 5, $R_1$ to $R_5$ may each independently be a hydrogen atom, a deuterium atom, a substituted or unsubstituted alkoxy group, a substituted or unsubstituted alkyl group of 1 to 60 carbon atoms, a substituted or unsubstituted alkenyl group of 2 to 60 carbon atoms, a substituted or unsubstituted alkynyl group of 2 to 60 carbon atoms, a substituted or unsubstituted aryl group of 6 to 60 ring-forming carbon atoms, a substituted or unsubstituted heteroaryl group of 1 to 60 ring-forming carbon atoms, or combined with an adjacent group to form a ring, $X_3$ and $X_4$ may make a direct linkage, and if $X_1$, $X_2$, $X_5$, and $X_6$ are all CH, then $R_1$ is may not be a hydrogen atom.

In an embodiment, Formula 1 may be represented by one of Formula 1-1 to Formula 1-3:

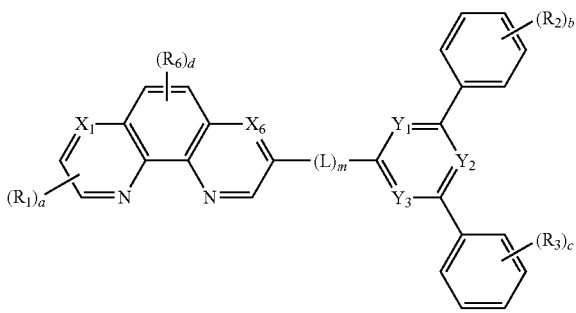

[Formula 1-1]

[Formula 1-2]

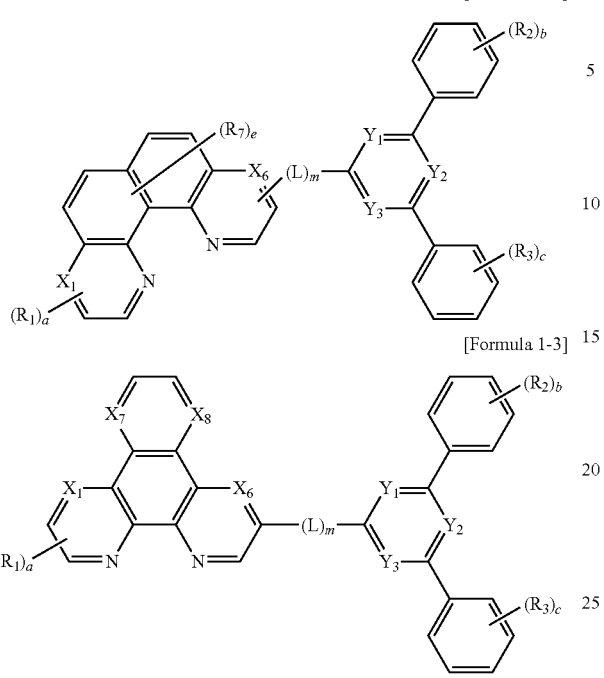

[Formula 1-3]

a deuterium atom, a substituted or unsubstituted alkoxy group, a substituted or unsubstituted alkyl group of 1 to 60 carbon atoms, a substituted or unsubstituted alkenyl group of 2 to 60 carbon atoms, a substituted or unsubstituted alkynyl group of 2 to 60 carbon atoms, a substituted or unsubstituted aryl group of 6 to 60 ring-forming carbon atoms, or a substituted or unsubstituted heteroaryl group of 1 to 60 ring-forming carbon atoms, and a to c, L, m, $R_1$ to $R_3$, $X_1$, $X_6$, and $Y_1$ to $Y_3$ may be the same as defined in Formula 1.

In an embodiment, Formula 1 may be represented by Formula 1-4:

[Formula 1-4]

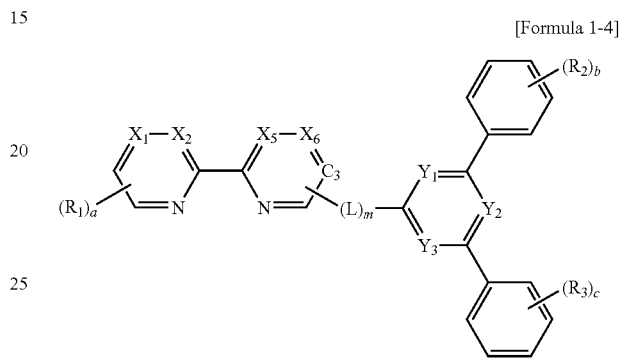

In Formula 1-1, d may be 1 or 2. In Formula 1-2, e may be an integer from 1 to 4. In Formula 1-3, $X_7$ and $X_8$ may each independently be N or $CR_8$. In Formula 1-1 to Formula 1-3, $R_6$ to $R_8$ may each independently be a hydrogen atom, In Formula 1-4, a to c, L, m, $R_1$ to $R_3$, $X_1$, $X_2$, $X_5$, $X_6$, $C_3$, and $Y_1$ to $Y_3$ may be the same as defined in Formula 1.

In an embodiment, Formula 1 may be represented by one of Formula 1-A to Formula 1-D:

[Formula 1-A]

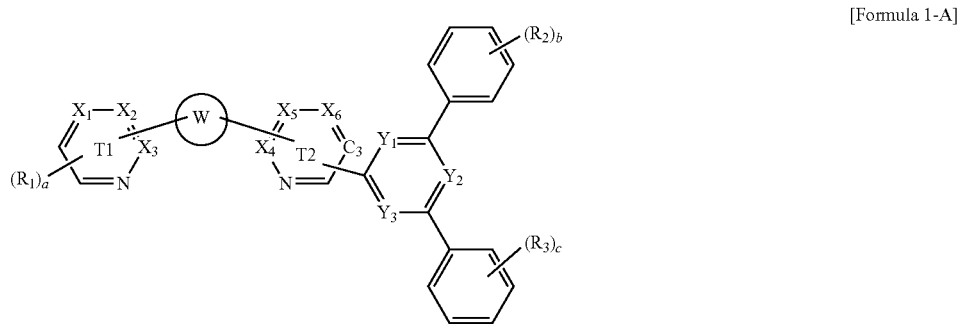

[Formula 1-B]

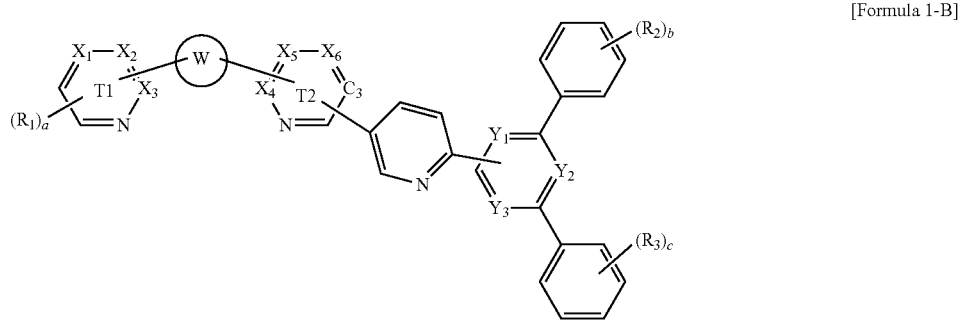

-continued

[Formula 1-C]

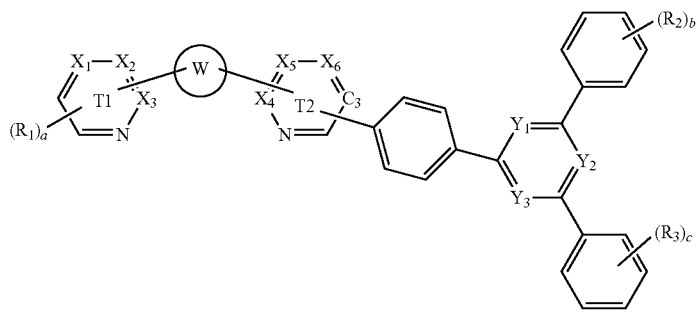

[Formula 1-D]

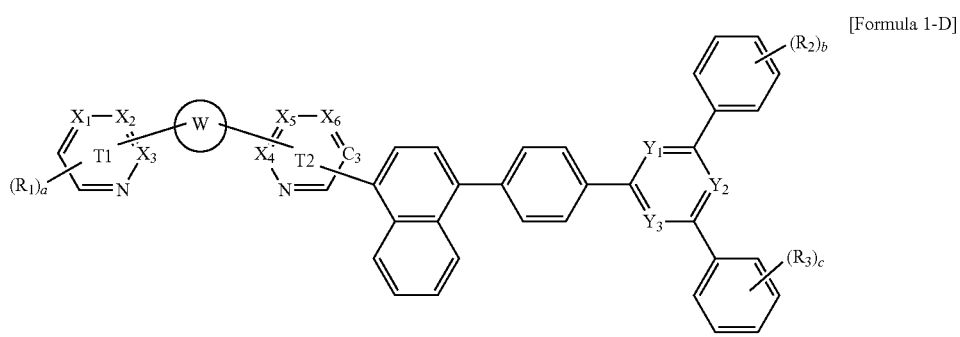

In Formula 1-A to Formula 1-D, a to c, $R_1$ to $R_3$, W, T1, T2, $X_1$ to $X_6$, $C_3$, and $Y_1$ to $Y_3$ may be the same as defined in Formula 1.

In an embodiment, $R_1$ may be a group represented by one of $R_{1-1}$ to $R_{1-4}$:

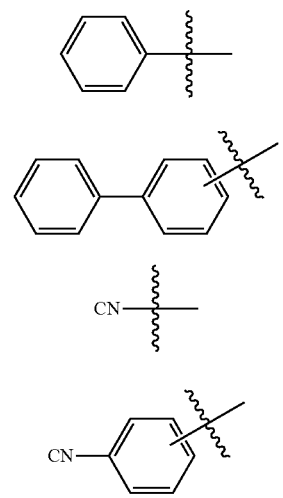

In an embodiment, the hole transport region may include a second compound represented by Formula 2:

[Formula 2]

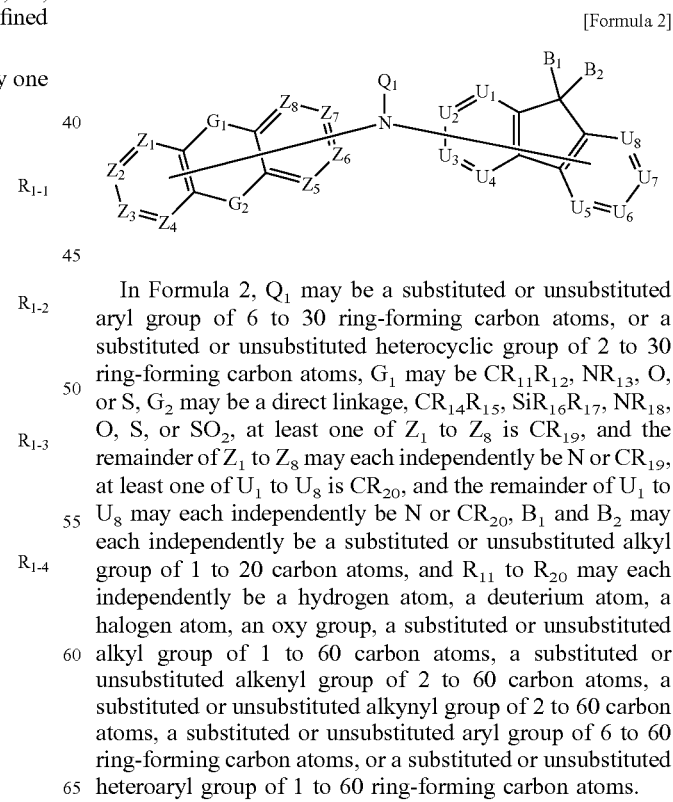

In Formula 2, $Q_1$ may be a substituted or unsubstituted aryl group of 6 to 30 ring-forming carbon atoms, or a substituted or unsubstituted heterocyclic group of 2 to 30 ring-forming carbon atoms, $G_1$ may be $CR_{11}R_{12}$, $NR_{13}$, O, or S, $G_2$ may be a direct linkage, $CR_{14}R_{15}$, $SiR_{16}R_{17}$, $NR_{18}$, O, S, or $SO_2$, at least one of $Z_1$ to $Z_8$ is $CR_{19}$, and the remainder of $Z_1$ to $Z_8$ may each independently be N or $CR_{19}$, at least one of $U_1$ to $U_8$ is $CR_{20}$, and the remainder of $U_1$ to $U_8$ may each independently be N or $CR_{20}$, $B_1$ and $B_2$ may each independently be a substituted or unsubstituted alkyl group of 1 to 20 carbon atoms, and $R_{11}$ to $R_{20}$ may each independently be a hydrogen atom, a deuterium atom, a halogen atom, an oxy group, a substituted or unsubstituted alkyl group of 1 to 60 carbon atoms, a substituted or unsubstituted alkenyl group of 2 to 60 carbon atoms, a substituted or unsubstituted alkynyl group of 2 to 60 carbon atoms, a substituted or unsubstituted aryl group of 6 to 60 ring-forming carbon atoms, or a substituted or unsubstituted heteroaryl group of 1 to 60 ring-forming carbon atoms.

In an embodiment, Formula 2 may be represented by Formula 2-1:

[Formula 2-1]

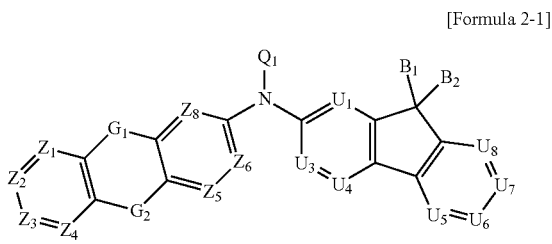

In Formula 2-1, $Q_1$, $B_1$, $B2$, $U_1$, $U_3$ to $U_8$, $G_1$, $G_2$, $Z_1$ to $Z_6$, and $Z_8$ may be the same as defined in Formula 2.

In an embodiment, $Q_1$ may be a group represented by one of $Q_{1-1}$ to $R_{1-5}$:

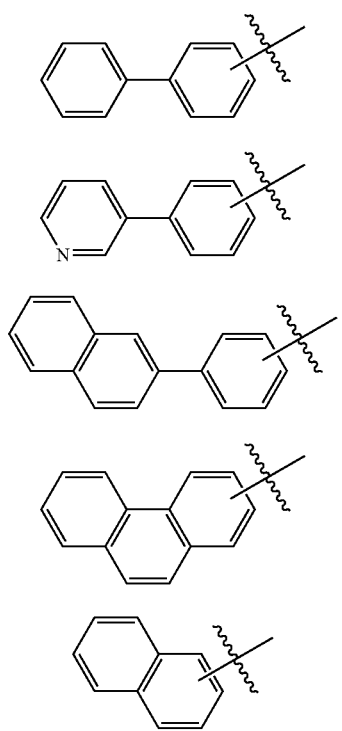

In an embodiment, $B_1$ and $B_2$ may be the same, and $B_1$ and $B_2$ may be unsubstituted alkyl groups of 2 to 10 carbon atoms.

In an embodiment, the hole transport region may include a hole injection layer, a first hole transport layer disposed on the hole injection layer, and a second hole transport layer disposed on the first hole transport layer. At least one of the hole injection layer, the first hole transport layer, and the second hole transport layer may include the second compound, and at least one of the hole injection layer and the second hole transport layer may include a p-dopant.

Another embodiment of the inventive concept provides an organic electroluminescence device including a first electrode, a second electrode disposed on the first electrode, light-emitting units disposed between the first electrode and the second electrode, and at least one charge generating layer disposed between two adjacent ones of the light-emitting units. The at least one charge generating layer may include a first compound represented by Formula 1.

In an embodiment, the light-emitting units may each include a hole transport region, an emission layer disposed on the hole transport region, and an electron transport region disposed on the emission layer. The electron transport region may include the first compound represented by Formula 1, and the hole transport region may include a second compound represented by Formula 2.

Another embodiment of the inventive concept provides a compound represented by Formula 1.

BRIEF DESCRIPTION OF THE DRAWINGS

The accompanying drawings are included to provide a further understanding of the inventive concept and are incorporated in and constitute a part of this specification. The drawings illustrate embodiments of the inventive concept and, together with the description, serve to explain principles of the inventive concept. In the drawings.

DETAILED DESCRIPTION OF THE EMBODIMENTS

Figure 1:
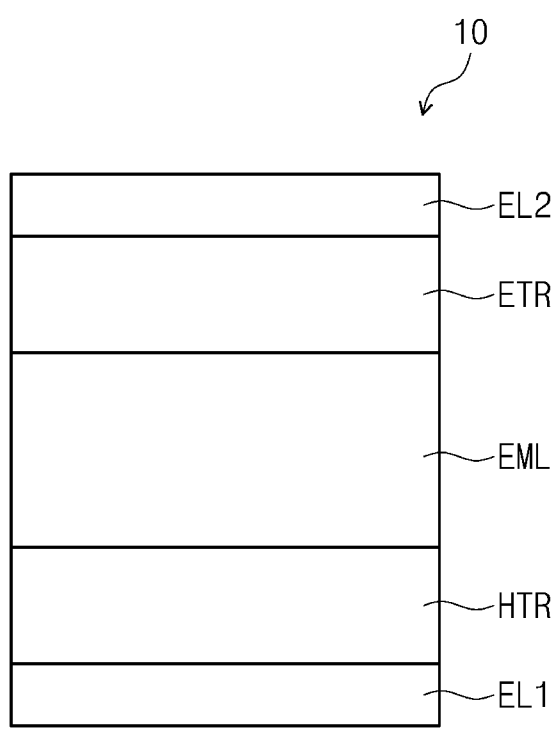
FIG. 1 is a schematic cross-sectional view illustrating an organic electroluminescence device according to an embodiment of the inventive concept.

The inventive concept may have various modifications and may be embodied in different forms, and example embodiments will be explained in detail with reference to the accompany drawings. The inventive concept may, however, be embodied in different forms and should not be construed as limited to the embodiments set forth herein. Rather, all modifications, equivalents, and substituents which are included in the spirit and technical scope of the inventive concept should be included in the inventive concept.

It will be understood that when an element (or region, layer, part, etc.) is referred to as being "on", "connected to" or "coupled to" another element, it can be directly on, connected or coupled to the other element or a third intervening elements may be present.

Like reference numerals refer to like elements throughout. In the drawings, the thickness, the ratio, and the dimensions of constituent elements may be exaggerated for effective explanation of technical contents.

As used herein, the term "and/or" includes any and all combinations of one or more of the associated listed items. For example, "A and/or B" may be understood to mean "A, B, or A and B." The terms "and" and "or" may be used in the conjunctive or disjunctive sense and may be understood to be equivalent to "and/or". Throughout the disclosure, the expression "at least one of A, B, and C" may indicate only A, only B, only C, both A and B, both A and C, both B and C, all of A, B, and C, or variations thereof.

The term "at least one of" is intended to include the meaning of "at least one selected from the group consisting of" for the purpose of its meaning and interpretation. For example, "at least one of A and B" may be understood to mean "A, B, or A and B." When preceding a list of elements, the term, "at least one of," modifies the entire list of elements and does not modify the individual elements of the list.

It will be understood that, although the terms "first", "second", etc. may be used herein to describe various elements, these elements should not be limited by these terms. These terms are only used to distinguish one element from another element. Thus, a first element could be termed a second element without departing from the teachings of the invention. Similarly, a second element could be termed a first element. As used herein, the singular forms are intended to include the plural forms as well, unless the context clearly indicates otherwise.

The terms "below", "beneath", "on" and "above" are used for explaining the relation of elements shown in the drawings. The terms are used as relative concept and are explained based on the direction shown in the drawing.

The terms "about" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" may mean within one or more standard deviations, or within ±20%, 10%, or 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It will be further understood that the terms "comprises," "comprising," "includes," "including," "have," "having," "contains," and/or "containing" when used in this specification, specify the presence of stated features, numerals, steps, operations, elements, parts, or the combination thereof, but do not preclude the presence or addition of one or more other features, numerals, steps, operations, elements, parts, or combinations thereof.

Hereinafter, an organic electroluminescence device according to an embodiment of the inventive concept and a compound of an embodiment, included therein will be explained with reference to attached drawings.

Figure 2:
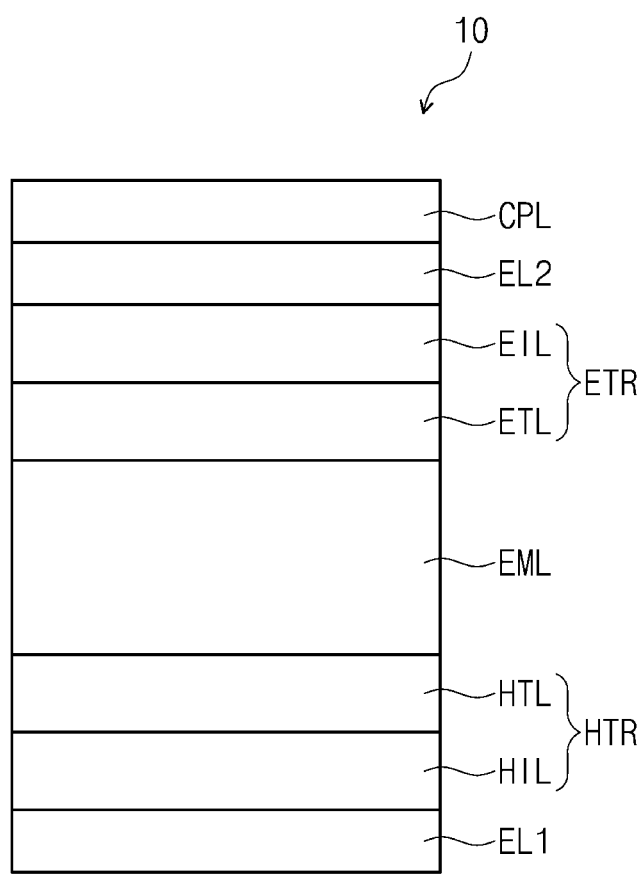
FIG. 2 is a schematic cross-sectional view illustrating an organic electroluminescence device according to an embodiment of the inventive concept.
Figure 3:
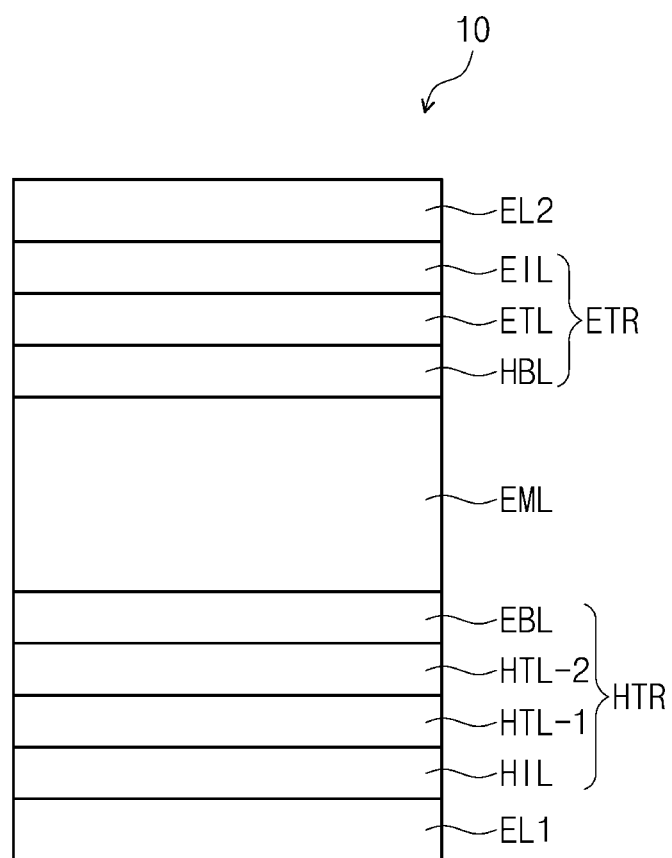
FIG. 3 is a schematic cross-sectional view illustrating an organic electroluminescence device according to an embodiment of the inventive concept.
Figure 4:
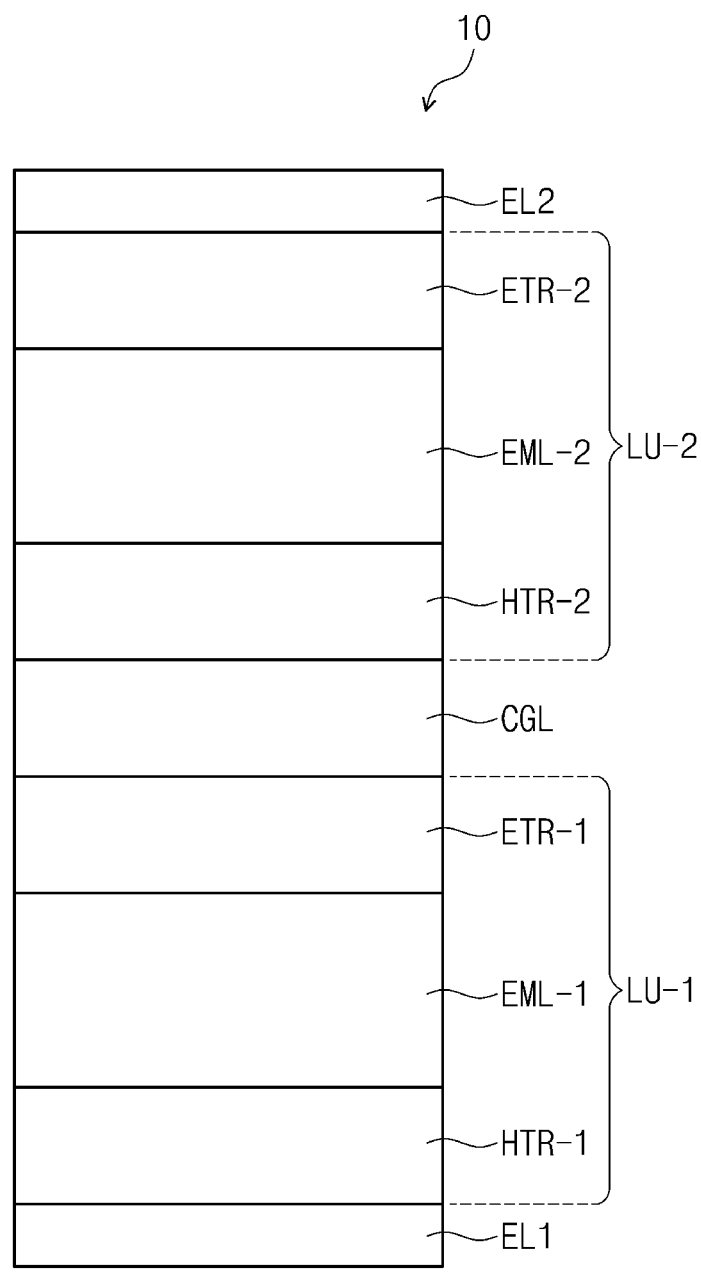
FIG. 4 is a schematic cross-sectional view illustrating an organic electroluminescence device according to an embodiment of the inventive concept.

FIG. 1 to FIG. 4 are schematic cross-sectional views schematically showing organic electroluminescence devices according to embodiments of the inventive concept. Referring to FIG. 1 to FIG. 4, in an organic electroluminescence device 10 according to an embodiment, a first electrode EL1 and a second electrode EL2 are oppositely disposed, and between the first electrode EL1 and the second electrode EL2, at least one emission layer EML, EML-1, or EML-2 may be disposed. In FIG. 4, in contrast to FIG. 1 to FIG. 3, an organic electroluminescence device including emission layers EML-1 and EML-2 is shown. In FIG. 4, light-emitting units LU-1 and LU-2, respectively including the emission layers EML-1 and EML-2 are shown.

An organic electroluminescence device 10 of an embodiment may further include functional layers between the first electrode EL1 and the second electrode EL2 in addition to the emission layers EML, EML-1, and EML-2. The functional layers may include hole transport regions HTR, HTR-1, and HTR-2 and electron transport regions ETR, ETR-1, and ETR-2. For example, the organic electroluminescence device 10 of an embodiment may include a first electrode EL1, hole transport regions HTR, HTR-1, and HTR-2, emission layers EML, EML-1, and EML-2, electron transport regions ETR, ETR-1, and ETR-2, and a second electrode EL2, which are disposed in sequence that will be explained in further detail below. The organic electroluminescence device 10 of an embodiment may include a capping layer CPL disposed on the second electrode EL2.

The organic electroluminescence device 10 of an embodiment may include the first compound of an embodiment, which will be explained later, in electron transport regions ETR, ETR-1, and ETR-2, disposed between the first electrode EL1 and the second electrode EL2. A charge generating layer CGL disposed between two adjacent ones of the light-emitting units LU-1 and LU-2 may include the first compound of an embodiment, which will be explained later. The light-emitting units LU-1 and LU-2, and the charge generating layer CGL will be explained in detail later.

In FIG. 1, an organic electroluminescence device 10 including a hole transport region HTR, an emission layer EML, and an electron transport region ETR is shown. In comparison to FIG. 1, FIG. 2 shows a schematic cross-sectional view of an organic electroluminescence device 10 of an embodiment, in which a hole transport region HTR includes a hole injection layer HIL and a hole transport layer HTL, an electron transport region ETR includes an electron injection layer EIL and an electron transport layer ETL, and a capping layer CPL disposed on the second electrode EL2 is included. In comparison to FIG. 1, FIG. 3 shows a schematic cross-sectional view of an organic electroluminescence device 10 of an embodiment, in which a hole transport region HTR includes a hole injection layer HIL, hole transport layers HTL-1 and HTL-2, and an electron blocking layer, and an electron transport region ETR includes an electron injection layer EIL, an electron transport layer ETL, and a hole blocking layer HBL. In comparison to FIG. 1, FIG. 4 shows a schematic cross-sectional view of an organic electroluminescence device 10 of an embodiment, including hole transport regions HTR-1 and HTR-2, emission layers EML-1 and EML-2, and electron transport regions ETR-1 and ETR-2.

The organic electroluminescence device 10 of an embodiment may include the first compound represented by Formula 1 in electron transport regions ETR, ETR-1, and ETR-2. As shown in FIG. 4, in the organic electroluminescence device 10 of an embodiment which includes light-emitting units LU-1 and LU-2, the first compound represented by Formula 1 may be included in any one of electron transport regions ETR-1 and ETR-2 and a charge generating layer CGL, or in both electron transport regions ETR-1 and ETR-2 and a charge generating layer CGL.

[Formula 1]

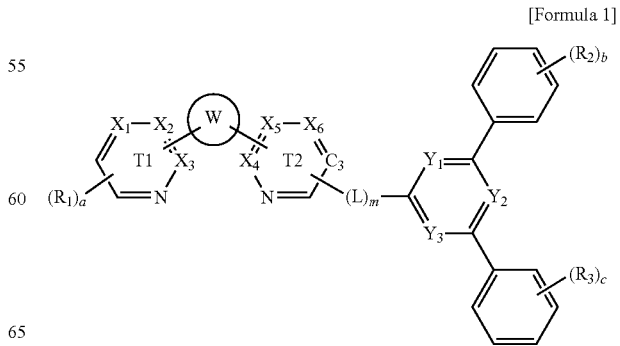

The first compound represented by Formula 1, and the electron transport regions ETR, ETR-1, and ETR-2 and the charge generating layer CGL including the first compound will be explained later.

The first electrode EL1 has conductivity. The first electrode EL1 may be formed using a metal alloy or a conductive compound. The first electrode EL1 may be an anode. The first electrode EL1 may be a pixel electrode. The first electrode EL1 may be a transmissive electrode, a transflective electrode, or a reflective electrode. If the first electrode EL1 is a transmissive electrode, the first electrode EL1 may be formed using a transparent metal oxide such as indium tin oxide (ITO), indium zinc oxide (IZO), zinc oxide (ZnO), and indium tin zinc oxide (ITZO). If the first electrode EL1 is a transflective electrode or a reflective electrode, the first electrode EL1 may include Ag, Mg, Cu, Al, Pt, Pd, Au, Ni, Nd, Jr, Cr, Li, Ca, LiF/Ca, LiF/Al, Mo, Ti, compounds thereof, or mixtures thereof (for example, a mixture of Ag and Mg). Also, the first electrode EL1 may have a structure including layers including a reflective layer or a transflective layer formed using the above materials, and a transmissive conductive layer formed using ITO, IZO, ZnO, or ITZO. For example, the first electrode EL1 may include a three-layer structure of ITO/Ag/ITO. However, an embodiment of the inventive concept is not limited thereto. The thickness of the first electrode EL1 may be in a range of about 1,000 Å to about 10,000 Å. For example, the thickness of the first electrode EL1 may be in a range of about 1,000 Å to about 3,000 Å.

Each of the hole transport regions HTR, HTR-1, and HTR-2 may be provided on the first electrode EL1. Each of the hole transport regions HTR, HTR-1, and HTR-2 may include at least one of a hole injection layer HIL, a hole transport layer HTL, a hole buffer layer (not shown), or an electron blocking layer EBL. The thickness of each of the hole transport regions HTR, HTR-1, and HTR-2 may be in a range of about 50 Å to about 15,000 Å.

Each of the hole transport regions HTR, HTR-1, and HTR-2 may have a single layer formed using a single material, a single layer formed using different materials, or a multilayer structure including multiple layers formed using different materials.

For example, each of the hole transport regions HTR, HTR-1, and HTR-2 may have the structure of a single layer of a hole injection layer HIL, or a hole transport layer HTL, and may have a structure of a single layer formed using a hole injection material and a hole transport material. Each of the hole transport regions HTR, HTR-1, and HTR-2 may have a structure of a single layer formed using different materials, or a structure stacked from the first electrode EL1 of hole injection layer HIL/hole transport layer HTL, hole injection layer HIL/hole transport layer HTL/hole buffer layer (not shown), hole injection layer HIL/hole buffer layer (not shown), hole transport layer HTL/hole buffer layer (not shown), hole injection layer HIL/hole transport layer HTL/ hole blocking layer EBL, or hole injection layer HIL/first hole transport layer HTL-1/second hole transport layer HTL-2/electron blocking layer EBL, without limitation.

The hole transport regions HTR, HTR-1, and HTR-2 may be formed using various methods such as a vacuum deposition method, a spin coating method, a cast method, a Langmuir-Blodgett (LB) method, an inkjet printing method, a laser printing method, and a laser induced thermal imaging (LITI) method.

The hole transport regions HTR, HTR-1, and HTR-2 may include a second compound of an embodiment. Any one of a hole injection layer HIL, the hole transport layers HTL, HTL-1, and HTL-2, and a hole buffer layer (not shown) may include the second compound of an embodiment. For example, the hole injection layer HIL may include a known material, and the hole transport layer HTL may include the second compound of an embodiment. Otherwise, the hole injection layer HIL may include the second compound of an embodiment, and the hole transport layers HTL, HTL-1, and HTL-2 may include a known material. Otherwise, the hole injection layer HIL and the first hole transport layer HTL-1 may include the second compound of an embodiment, and the second hole transport layer HTL-2 may include a known material. However, these are only embodiments, and embodiments of the inventive concept are not limited thereto.

In the description, the term "substituted or unsubstituted" corresponds to substituted or unsubstituted with at least one substituent selected from the group consisting of a deuterium atom, a halogen atom, a hydroxyl group, an amidino group, a hydrazino group, a hydrazono group, a carboxylic acid group, a cyano group, a nitro group, an amino group, a silyl group, an oxy group, a thio group, a sulfinyl group, a sulfonyl group, a carbonyl group, a boron group, a phosphine group, a phosphine oxide group, a phosphine sulfide group, an alkyl group, an alkenyl group, an alkynyl group, an alkoxy group, a hydrocarbon ring group, an aryl group, and a heterocyclic group. Each of the substituents may be substituted or unsubstituted. For example, a biphenyl group may be interpreted as an aryl group or a phenyl group substituted with a phenyl group.

In the description, the term "forming a ring via the combination with an adjacent group" may mean forming a substituted or unsubstituted hydrocarbon ring, or a substituted or unsubstituted heterocycle via the combination with an adjacent group. The hydrocarbon ring includes an aliphatic hydrocarbon ring and an aromatic hydrocarbon ring. The heterocycle includes an aliphatic heterocycle and an aromatic heterocycle. The ring formed by the combination with an adjacent group may be a monocyclic ring or a polycyclic ring. The ring formed via the combination with an adjacent group may be combined with another ring to form a spiro structure.

In the description, the term "adjacent group" may mean a substituent substituted for an atom which is directly combined with an atom substituted with a corresponding substituent, another substituent substituted for an atom which is substituted with a corresponding substituent, or a substituent sterically positioned at the nearest position to a corresponding substituent. For example, in 1,2-dimethylbenzene, two methyl groups may be interpreted as "adjacent groups" to each other, and in 1,1-diethylcyclopentene, two ethyl groups may be interpreted as "adjacent groups" to each other.

In the description, examples of the halogen atom may include a fluorine atom, a chlorine atom, a bromine atom, or an iodine atom.

In the description, the alkyl may be a linear, branched, or cyclic type. The carbon number of the alkyl may be 1 to 50, 1 to 30, 1 to 20, 1 to 10, or 1 to 6. Examples of the alkyl may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the description, the aryl group means an optional functional group or substituent derived from an aromatic hydrocarbon ring. The aryl group may be a monocyclic aryl group or a polycyclic aryl group. The carbon number for forming a ring in the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinquephenyl, sexiphenyl, triphenylenyl, pyrenyl, benzofluoranthenyl, chrysenyl, etc., without limitation.

In the description, the heterocyclic group means an optional functional group or substituent derived from a ring including one or more among B, O, N, P, Si and S as heteroatoms. If the heterocyclic group includes two or more heteroatoms, the two or more heteroatoms may be the same or different from each other. The heterocyclic group includes an aliphatic heterocyclic group and an aromatic heterocyclic group. The aromatic heterocyclic group may be a heteroaryl group. The aliphatic heterocycle and the aromatic heterocycle may be a monocycle or a polycycle.

In the description, the heteroaryl group may include one or more among B, O, N, P, Si and S as heteroatoms. If the heteroaryl group includes two or more heteroatoms, the two or more heteroatoms may be the same or different from each other. The heteroaryl group may be a monocyclic heterocyclic group or a polycyclic heterocyclic group. The carbon number for forming a ring of the heteroaryl group may be 2 to 30, 2 to 20, or 2 to 10. Examples of the heteroaryl group may include thiophene, furan, pyrrole, imidazole, triazole, pyridine, bipyridine, pyrimidine, triazine, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofurane, phenanthroline, thiazole, isooxazole, oxazole, oxadiazole, thiadiazole, phenothiazine, dibenzosilole, dibenzofuran, etc., without limitation.

In the description, the oxy group may include an alkoxy group and an aryl oxy group. The alkoxy group may be a linear chain, a branched chain, or a cyclic chain. The carbon number of the alkoxy group is not specifically limited, but may be, for example, 1 to 20, or 1 to 10. Examples of the oxy group include methoxy, ethoxy, n-propoxy, isopropoxy, butoxy, pentyloxy, hexyloxy, octyloxy, nonyloxy, decyloxy, benzyloxy, etc., without limitation.

In the description, the alkenyl group may be a linear chain, a branched chain, or a cyclic type. The carbon number is not specifically limited, but is 2 to 30, 2 to 20 or 2 to 10. Examples of the alkenyl group include a vinyl group, a 1-butenyl group, a 1-pentenyl group, a 1,3-butadienyl aryl group, a styrenyl group, a styrylvinyl group, etc., without limitation.

In the description, the alkynyl group means a hydrocarbon group including one or more carbon triple bonds in the middle of or at the terminal of an alkyl group of 2 or more carbon atoms. The alkynyl group may be a linear chain, a branched chain, or a cyclic type. The carbon number is not specifically limited, but is 2 to 30, 2 to 20 or 2 to 10. Examples of the alkynyl group include an ethynyl group, a propynyl group, etc., without limitation.

In the description, a direct linkage may mean a single bond.

In the description,

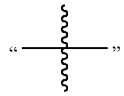

means a binding site to a neighboring atom.

The hole transport regions HTR, HTR-1, and HTR-2 of an embodiment may include a second compound represented by the following Formula 2:

[Formula 2]

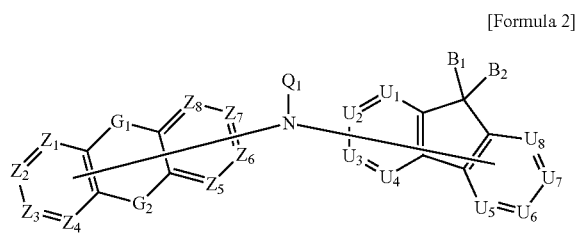

In Formula 2, $Q_1$ may be a substituted or unsubstituted aryl group of 6 to 30 ring-forming carbon atoms, or a substituted or unsubstituted heterocyclic group of 2 to 30 ring-forming carbon atoms. $Q_1$ may be represented by one of the following $Q_{1-1}$ to $Q_{1-5}$:

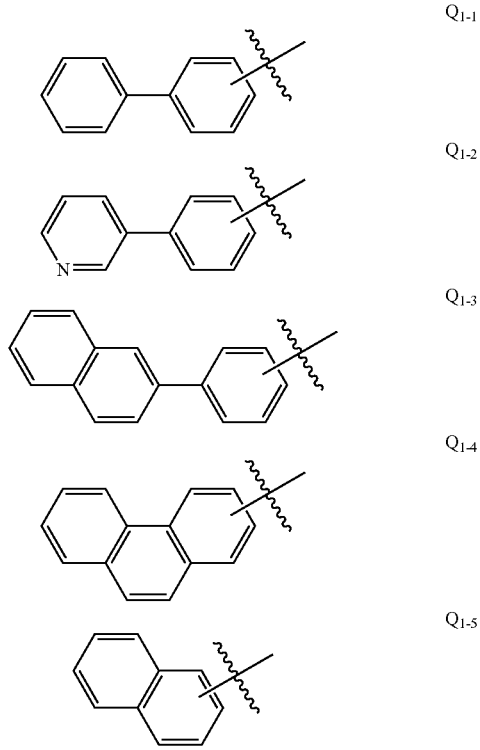

$G_1$ may be $CR_{11}R_{12}$, $NR_{13}$, O, or S. $G_2$ may be a direct linkage, $CR_{14}R_{15}$, $SiR_{16}R_{17}$, $NR_{18}$, O, S, or $SO_2$. For example, $G_1$ may include a methyl group, an oxygen atom, or a nitrogen atom, and $G_2$ may be a direct linkage. Otherwise, $G_1$ may be an oxygen atom, and $G_2$ may include a carbon atom. However, an embodiment of the inventive concept is not limited thereto.

At least one of $Z_1$ to $Z_8$ may be $CR_{19}$, and the remainder of $Z_1$ to $Z_8$ may each independently be N or $CR_{19}$. At least one of $U_1$ to $U_8$ may be $CR_{20}$, and the remainder of $U_1$ to $U_8$ may each independently be N or $CR_{20}$. For example, $Z_1$ to $Z_8$, and $U_1$ to $U_8$ all may include a carbon atom.

$B_1$ and $B_2$ may each independently be a substituted or unsubstituted alkyl group of 1 to 20 carbon atoms. In an embodiment, $B_1$ and $B_2$ may be the same, and $B_1$ and $B_2$ may be unsubstituted alkyl groups of 2 to 10 carbon atoms. $B_1$ and $B_2$ may be the same and a butyl group or a hexyl group. However, an embodiment of the inventive concept is not limited thereto.

$R_{11}$ to $R_{20}$ may each independently be a hydrogen atom, a deuterium atom, a halogen atom, an oxy group, a substituted or unsubstituted alkyl group of 1 to 60 carbon atoms, a substituted or unsubstituted alkenyl group of 2 to 60 carbon atoms, a substituted or unsubstituted alkynyl group of 2 to 60 carbon atoms, a substituted or unsubstituted aryl group of 6 to 60 ring-forming carbon atoms, or a substituted or unsubstituted heteroaryl group of 1 to 60 ring-forming carbon atoms.

Formula 2 may be represented by the following Formula 2-1:

[Formula 2-1]

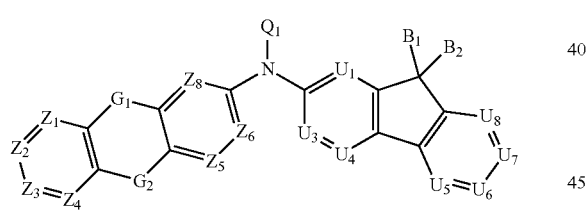

Formula 2-1 represents an embodiment where a nitrogen atom bonded to $Q_1$ is bonded to a carbon atom of $Z_7$ and $U_2$. The same explanation on $Q_1$, $B_1$, $B_2$, $U_1$, $U_3$ to $U_8$, $G_1$, $G_2$, $Z_1$ to $Z_6$, and $Z_8$ in reference to Formula 2 may be applied to each in Formula 2-1.

The second compound of an embodiment represented by Formula 2 may be one selected from Compound Group 2, which includes Compounds 2-1 to 2-16. For example, the organic electroluminescence device 10 of an embodiment may include one of the second compounds represented in the following Compound Group 2 in hole transport regions HTR, HTR-1, and HTR-2:

[Compound Group 2]

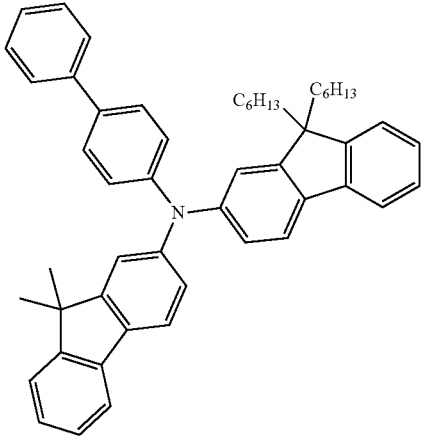

2-1

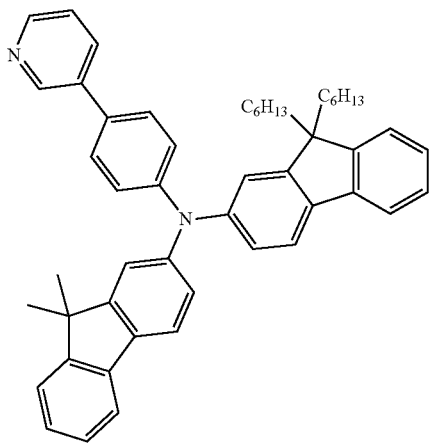

2-2

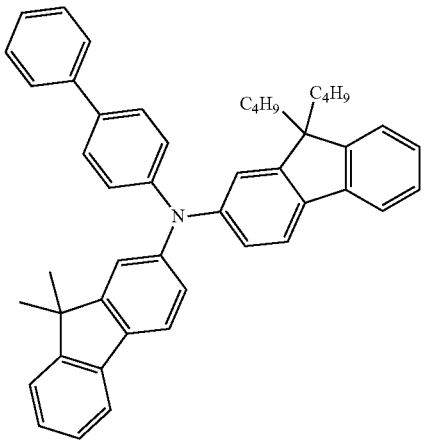

2-3

2-4
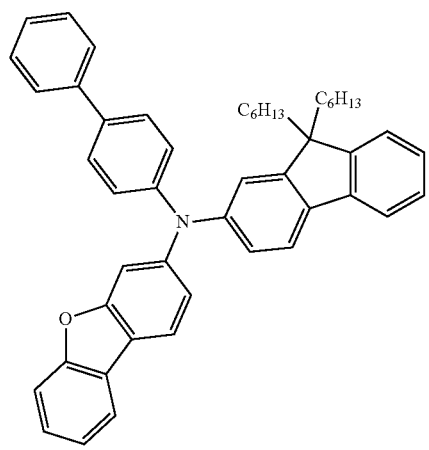
2-5
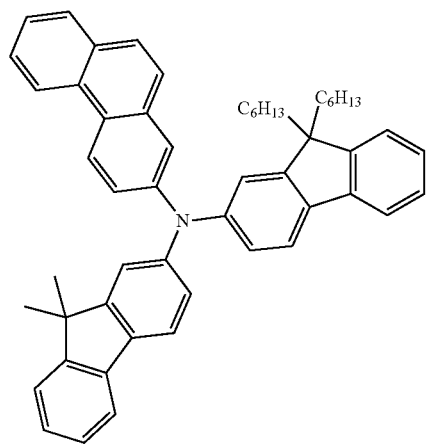
2-6
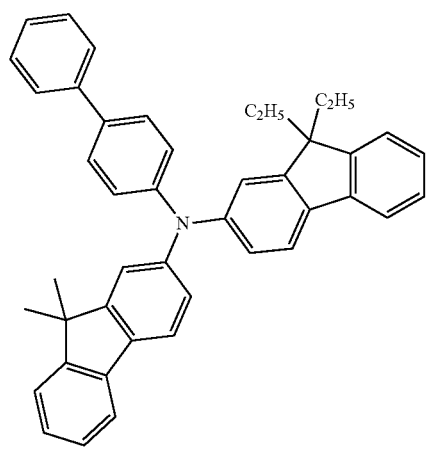
2-7
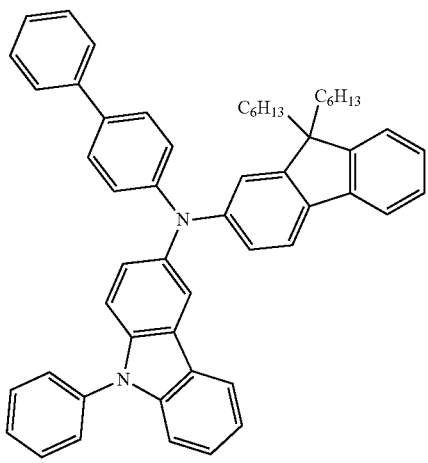
2-8
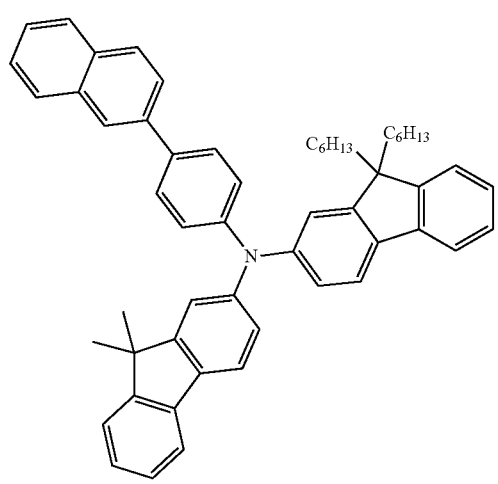
2-9
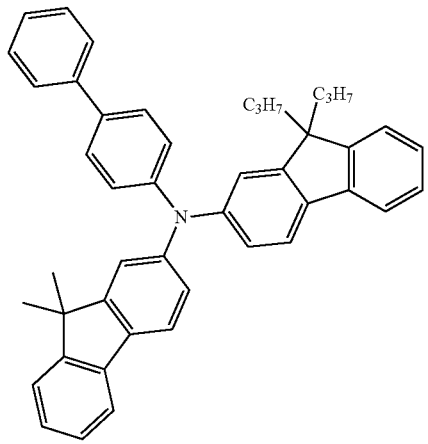

-continued
2-10
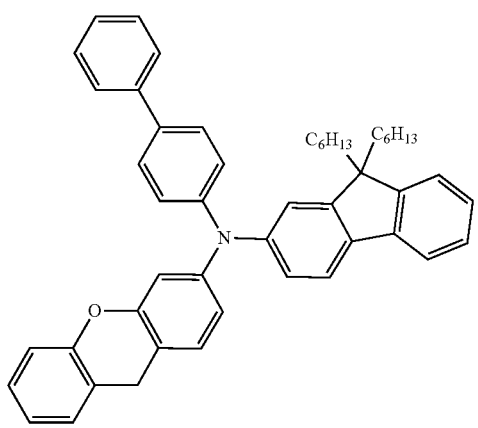
2-13
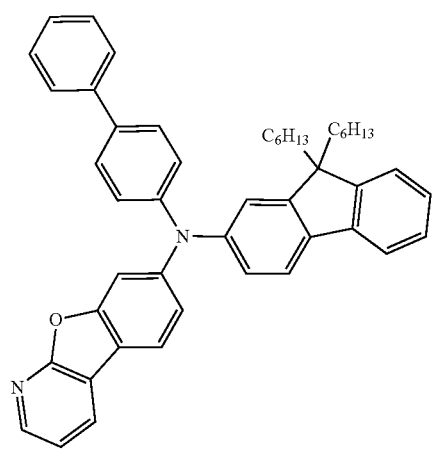
2-11
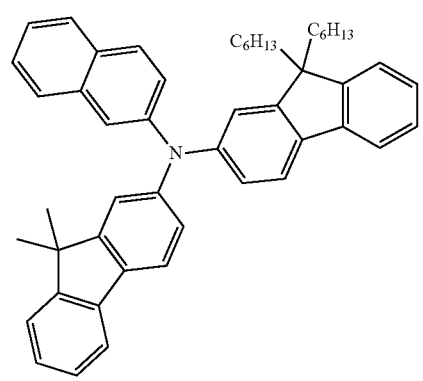
2-14
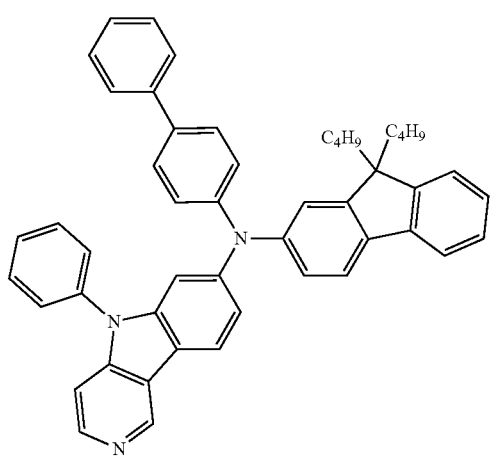
2-12
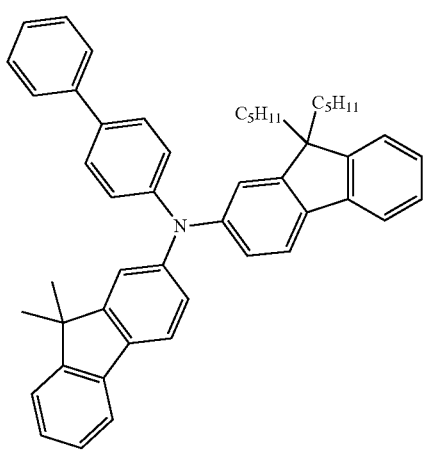
2-15
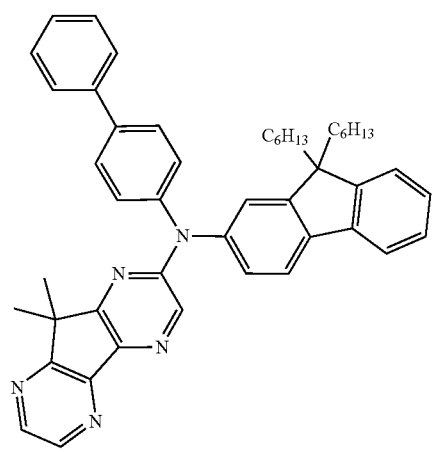

-continued 2-16

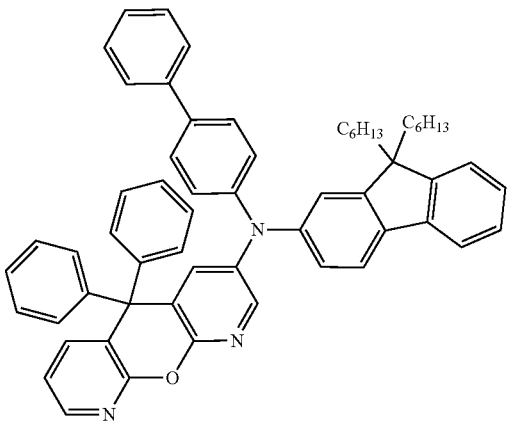

The hole injection layer HIL may include, for example, a phthalocyanine compound such as copper phthalocyanine, N,N'-diphenyl-N,N'-bis-[4-(phenyl-m-tolyl-amino)-phenyl]-biphenyl-4,4'-diamine (DNTPD), 4,4',4"-[tris(3-methylphenyl)phenylamino] triphenylamine (m-MTDATA), 4,4',4"-tris(N,N-diphenylamino)triphenylamine (TDATA), 4,4',4"-tris{N,-2-naphthyl)-N-phenylamino}-triphenylamine (2-TNATA), poly(3,4-ethylenedioxythiophene)/poly(4-styrene sulfonate) (PEDOT/PSS), polyaniline/dodecylbenzenesulfonic acid (PANI/DBSA), polyaniline/camphor sulfonic acid (PANI/CS A), poly aniline/poly(4-styrenesulfonate) (PANI/PSS), N,N'-di(1-naphthalene-1-yl)-N,N'-diphenyl-benzidine (NPB), triphenylamine-containing polyetherketone (TPAPEK), 4-isopropyl-4'-methyldiphenyliodonium [tetrakis(pentafluorophenyl)borate], and dipyrazino [2,3-f: 2',3'-h]quinoxaline-2,3,6,7,10,11-hexacarbonitrile (HAT-CN).

The hole transport layers HTL, HTL-1, and HTL-2 may include, for example, carbazole derivatives such as N-phenyl carbazole and polyvinyl carbazole, fluorene-based derivatives, N,N'-bis(3-methylphenyl)-N,N'-diphenyl-[1,1-biphenyl]-4,4'-diamine (TPD), triphenylamine-based derivatives such as 4,4',4"-tris(N-carbazolyl)triphenylamine (TCTA), N,N'-di(1-naphthalene-1-yl)-N,N'-diphenyl-benzidine (NPB), 4,4'-cyclohexylidene bis[N,N-bis(4-methylphenyl)benzeneamine (TAPC), 4,4'-b s[N,N'-(3-tolyl)amino]-3,3'-dimethylbiphenyl (HMTPD), 1,3-bis(N-carbazolyl) benzene (mCP), etc.

The thicknesses of each of the hole transport regions HTR, HTR-1, and HTR-2 may be in a range of about 50 Å to about 10,000 Å. For example, the thicknesses of each of the hole transport regions HTR, HTR-1, and HTR-2 may be in a range of about 100 Å to about 5,000 Å. The thickness of the hole injection region HIL may be, for example, in a range of about 30 Å to about 1,000 Å, and the thickness of the hole transport layer HTL may be in a range of about 30 Å to about 1,000 Å. For example, the thickness of the electron blocking layer EBL may be in a range of about 10 Å to about 1,000 Å. If the thicknesses of the hole transport regions HTR, HTR-1, and HTR-2, the hole injection layer HIL, the hole transport layer HTL, and the electron blocking layer EBL satisfy the above-described ranges, satisfactory hole transport properties may be achieved without substantial increase of a driving voltage.

The hole transport regions HTR, HTR-1, and HTR-2 may further include a charge generating material in addition to the above-described materials to increase conductivity. The charge generating material may be dispersed uniformly or non-uniformly in the hole transport regions HTR, HTR-1, and HTR-2. The charge generating material may be, for example, a p-dopant. The p-dopant may be included in at least one layer among the hole transport regions HTR, HTR-1, and HTR-2, except for hole transport layers HTL and HTL-1. For example, the p-dopant may be included in the hole injection layer HIL or the second hole transport layer HTL-2. However, an embodiment of the inventive concept is not limited thereto.

The p-dopant may be one of quinone derivatives, metal oxides, or cyano group-containing compounds, without limitation. For example, non-limiting examples of the p-dopant may include quinone derivatives such as tetracyanoquinodimethane (TCNQ) and 2,3,5,6-tetrafluoro-7,7',8,8'-tetracyanoquinodimethane (F4-TCNQ), metal oxides such as tungsten oxide, and molybdenum oxide, without limitation.

As described above, each of the hole transport regions HTR, HTR-1, and HTR-2 may further include at least one of a hole buffer layer (not shown) or an electron blocking layer EBL in addition to the hole injection layer HIL and the hole transport layers HTL, HTL-1, and HTL-2. The hole buffer layer (not shown) may compensate an optical resonance distance according to the wavelength of light emitted from emission layers EML, EML-1, and EML-2 and may increase light emission efficiency. Materials which may be included in hole transport regions HTR, HTR-1, and HTR-2 may be used as materials included in a hole buffer layer (not shown). The electron blocking layer EBL is a layer that may prevent the injection of electrons from the electron transport regions ETR, ETR-1, and ETR-2 to the hole transport regions HTR, HTR-1, and HTR-2.

If the organic electroluminescence device of an embodiment emits blue light, then a blue auxiliary layer (not shown) disposed between the hole transport layer HTL and the emission layer EML may be further included. The blue auxiliary layer (not shown) may control hole charge balance to improve the light generation efficiency of the emission layer EML of the organic electroluminescence device. However, an embodiment of the inventive concept is not limited thereto, and the organic electroluminescence device of another embodiment of the inventive concept may emit other color light different from the blue light.

Each of the emission layers EML, EML-1, and EML-2 is provided on each of the hole transport regions HTR, HTR-1, and HTR-2. Each of the emission layers EML, EML-1, and EML-2 may have a thickness in a range of about 100 Å to about 1,000 Å. For example, the emission layers EML, EML-1, and EML-2 may each have a thickness in a range of about 100 Å to about 400 Å. Each of the emission layers EML, EML-1, and EML-2 may have a single layer formed using a single material, a single layer formed using different materials, or a multilayer structure having multiple layers formed using different materials.

In the organic electroluminescence device 10 of an embodiment, the emission layers EML, EML-1, and EML-2 may include anthracene derivatives, pyrene derivatives, fluoranthene derivatives, chrysene derivative, dihydrobenz anthracene derivatives, or triphenylene derivatives. The emission layers EML, EML-1, and EML-2 may include anthracene derivatives or pyrene derivatives.

The emission layers EML, EML-1, and EML-2 may include an anthracene derivative represented by the following Formula A:

[Formula A]

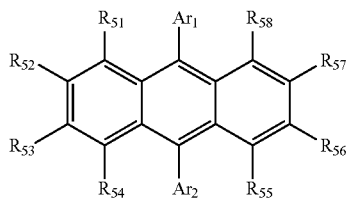

In Formula A, $Ar_1$ and $Ar_2$ may each independently be a substituted or unsubstituted aryl group of 6 to 30 ring-forming carbon atoms, or a substituted or unsubstituted heteroaryl group of 2 to 30 ring-forming carbon atoms.

In Formula A, $R_{51}$ to $R_{58}$ may each independently be a hydrogen atom, a deuterium atom, a substituted or unsubstituted alkyl group of 1 to 60 carbon atoms, a substituted or unsubstituted aryl group of 6 to 60 ring-forming carbon atoms, a substituted or unsubstituted heteroaryl group of 1 to 60 ring-forming carbon atoms, or combined with an adjacent group to form a ring. For example, $R_{51}$ to $R_{58}$ may each independently be combined with an adjacent group to form a saturated hydrocarbon ring or an unsaturated hydrocarbon ring.

Formula A may be represented by one of the following Compound A-1 to Compound A-16:

A-1
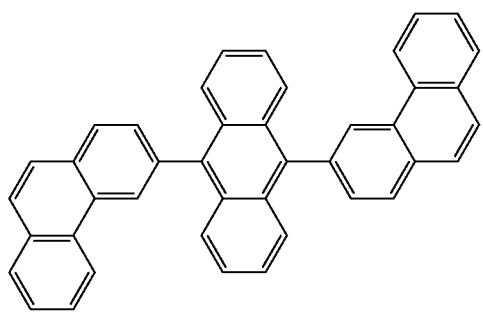

A-2
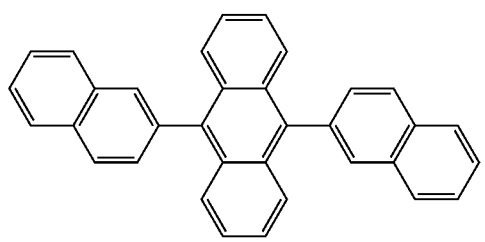

A-3
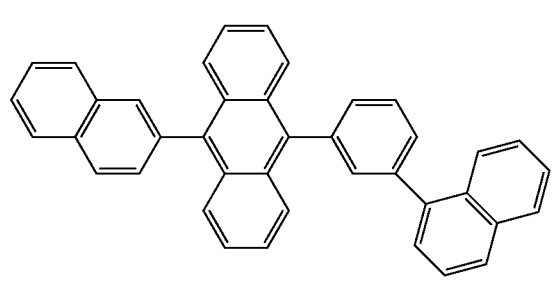

A-4
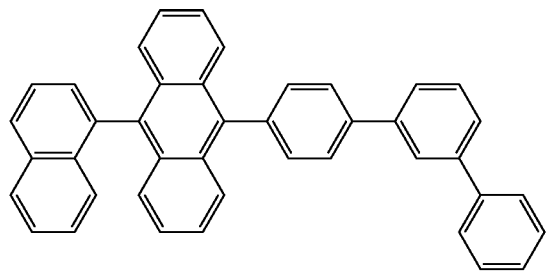

A-5

A-6
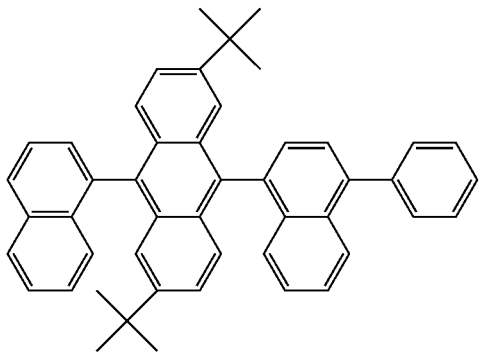

A-7
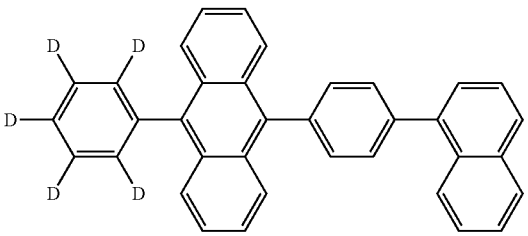

A-8
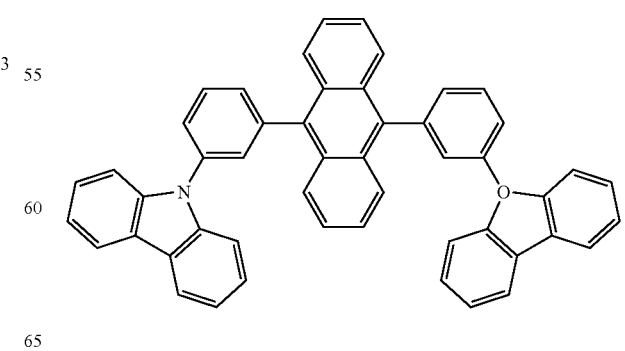

-continued

A-9
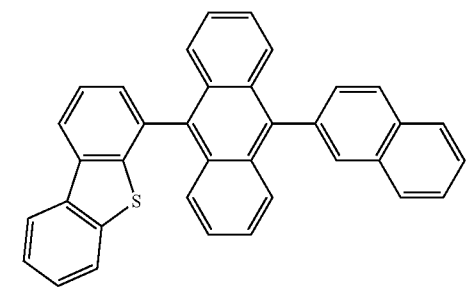

A-10
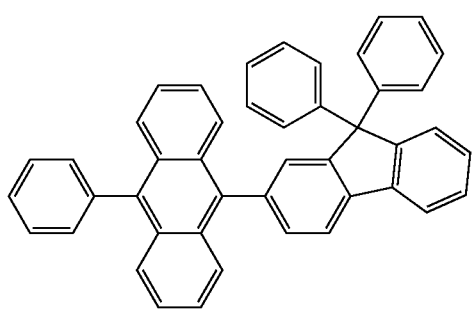

A-11
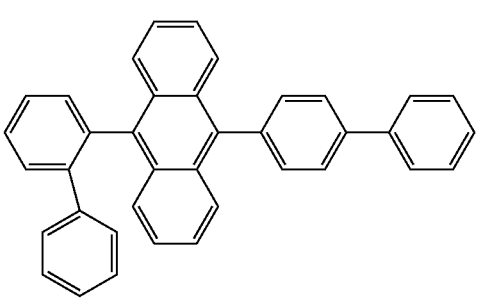

A-12
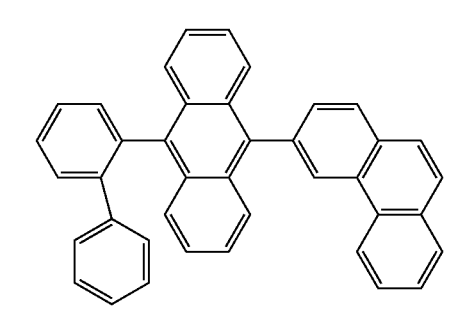

A-13
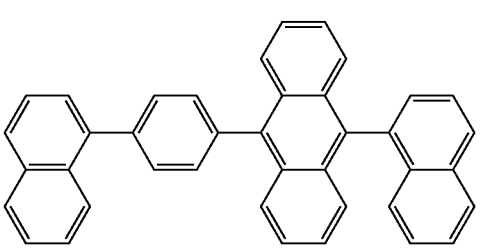

-continued

A-14
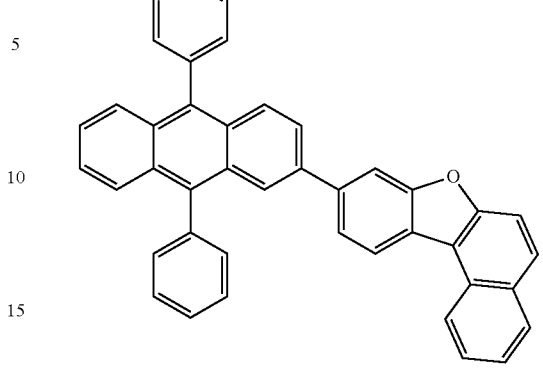

A-15
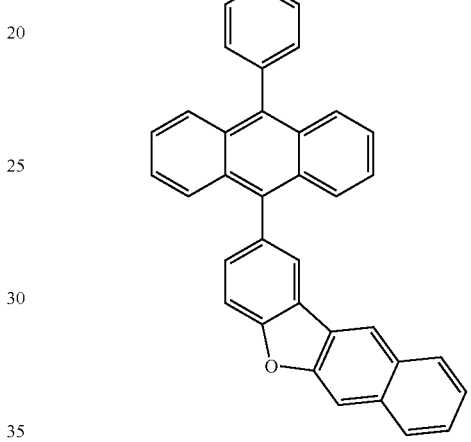

A-16
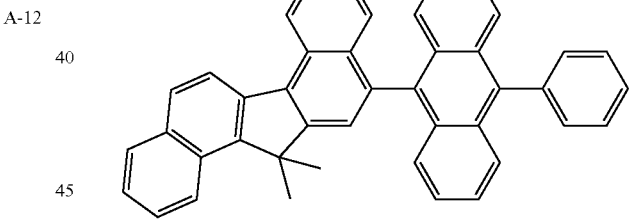

In the organic electroluminescence devices 10 of embodiments, as shown in FIG. 1 to FIG. 4, the emission layers EML, EML-1, and EML-2 may include a host and a dopant, and the emission layers EML, EML-1, and EML-2 may include the compound represented by Formula A as a host material.

In an embodiment, the emission layers EML, EML-1, and EML-2 may include common materials well-known in the art as the host material. For example, the emission layers EML, EML-1, and EML-2 may include as a host material, tris(8-hydroxyquinolino)aluminum (Alq$_3$), 4,4'-bis(N-carbazolyl)-1,1'-biphenyl (CBP), poly(N-vinylcarbazole) (PVK), 9,10-di(naphthalene-2-yl)anthracene (ADN), 4,4',4"-tris(carbazol-9-yl)-triphenylamine (TCTA), 1,3,5-tris(N-phenyl-1H-benzo[d]imidazole-2-yl)benzene (TPBi), 3-tert-butyl-9,10-di(naphth-2-yl)anthracene (TBADN), di styryl aryl ene (DSA), 4,4'-bis(9-carbazolyl)-2,2"-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane (DPSiO$_3$), octaphenylcyclotetrasiloxane (DPSiO$_4$), 2,8-bis(diphenylphosphoryl)dibenzofuran (PPF), 3,3'-bis(N-carbazolyl)-1,1'-biphenyl(mCBP), 1,3-bis(N-carbazolyl)benzene (mCP), etc.

In the organic electroluminescence device 10 of an embodiment, the emission layers EML, EML-1, and EML-2 may include as a dopant material, styryl derivatives (for example, 1,4-bis [2-(3-N-ethylcarbazoryl)vinyl]benzene (BCzVB), 4-(di-p-tolylamino)-4'-[(di-p-tolylamino)styryl] stilbene (DPAVB), and N-(4-((E)-2-(6-((E)-4-(diphenylamino)styryl)naphthalen-2-yl)vinyl)phenyl)-N-phenyl-benzenamine (N-BDAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, and 1,4-bis(N,N-diphenylamino)pyrene), etc.

The emission layers EML, EML-1, and EML-2 may include one of the compounds selected from Compound Group D, which includes Compounds D1 to D33. However, an embodiment of the inventive concept is not limited thereto.

[Compound Group D]

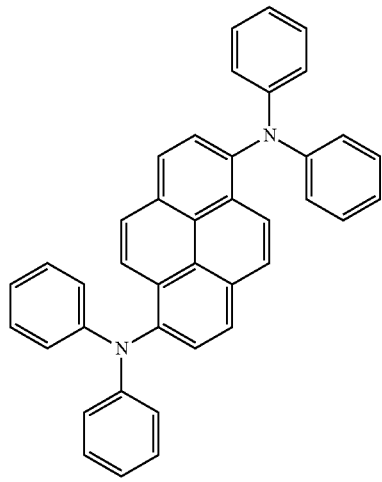

D1

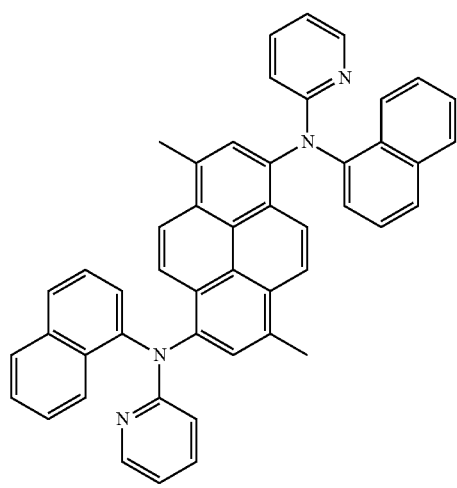

D2

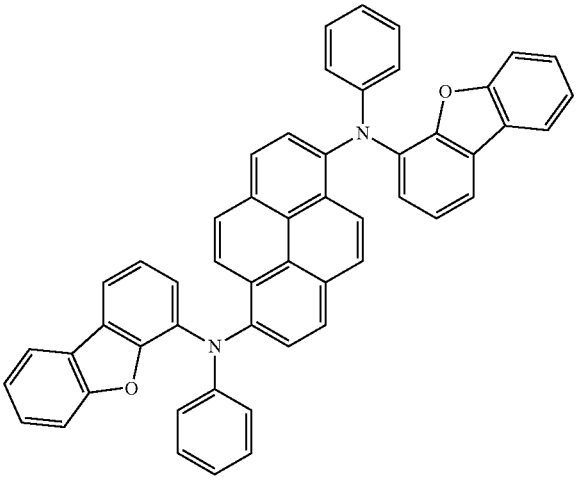

D3

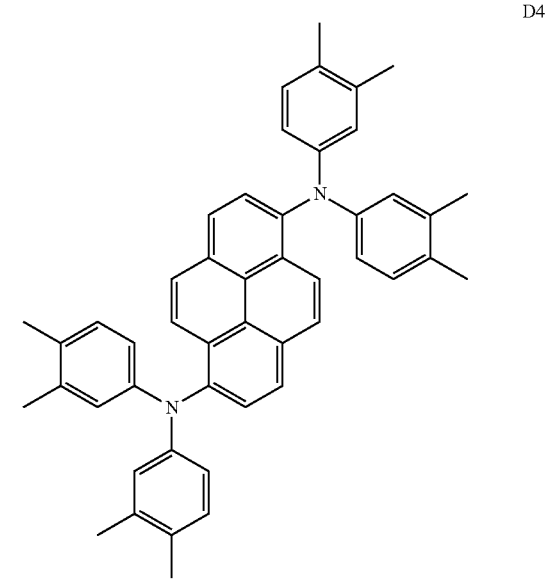

D4

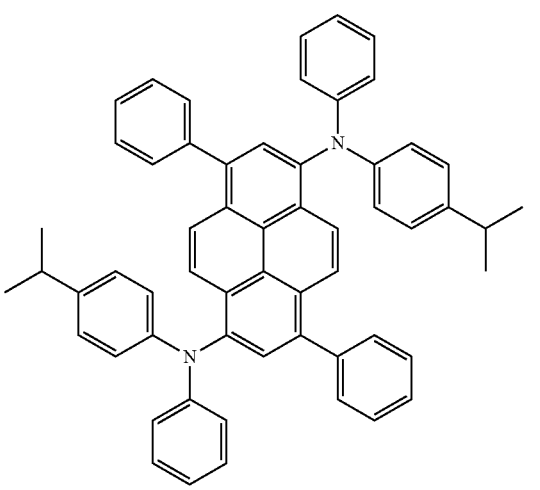

D5

D6
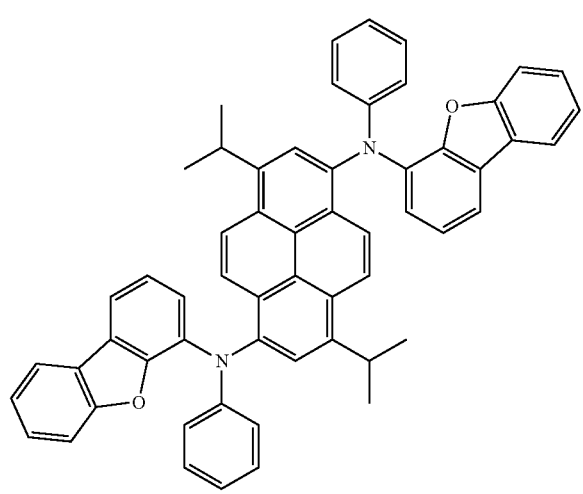
D7
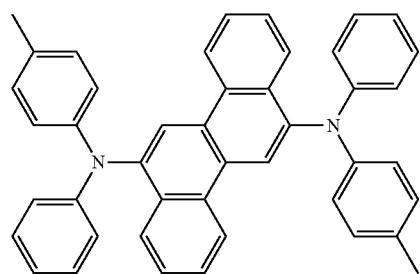
D8
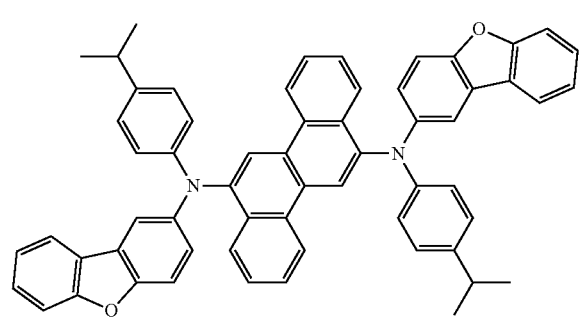
D9
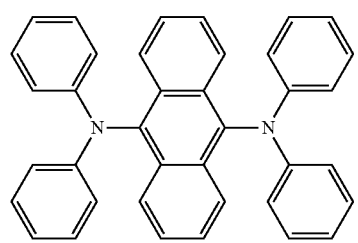
D10
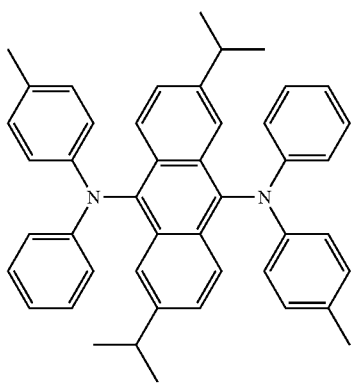
D11
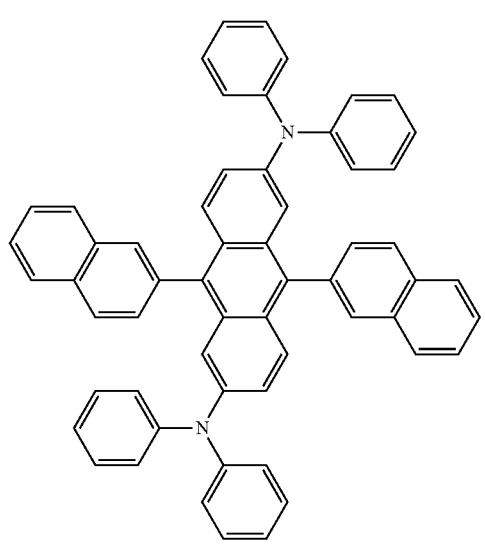
D12
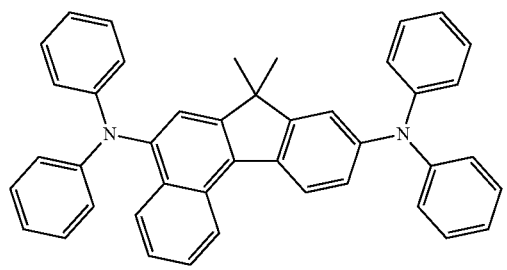
D13
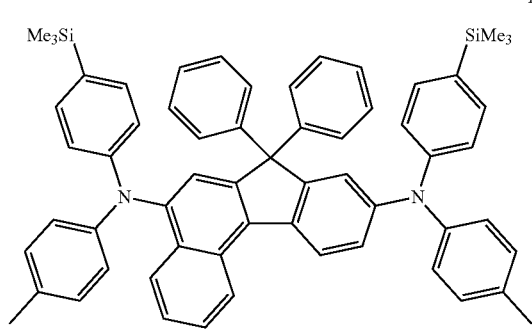

D14
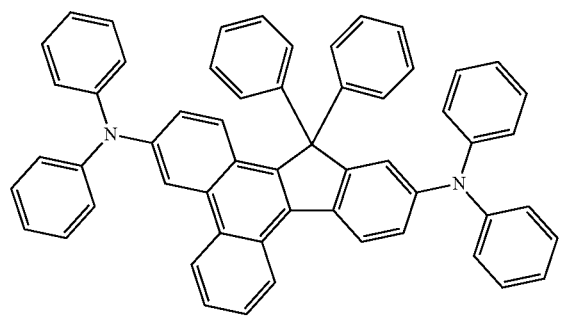
D15
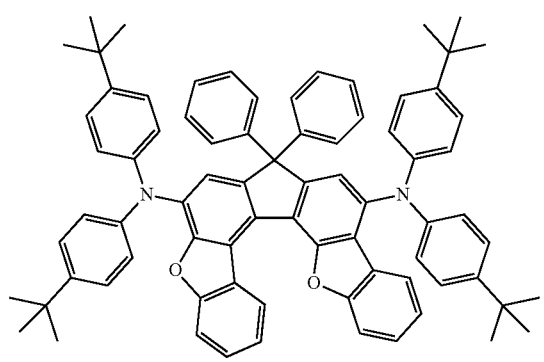
D16
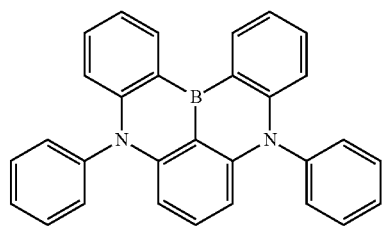
D17
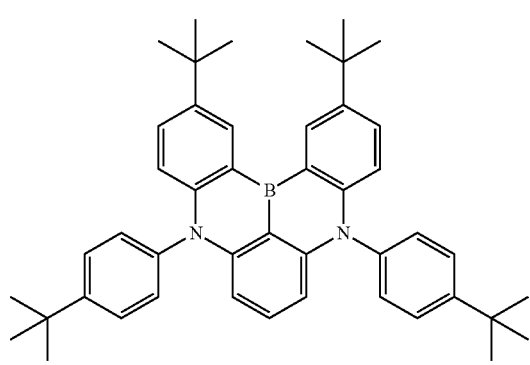
D18
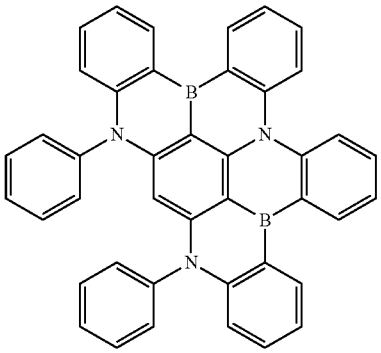
D18
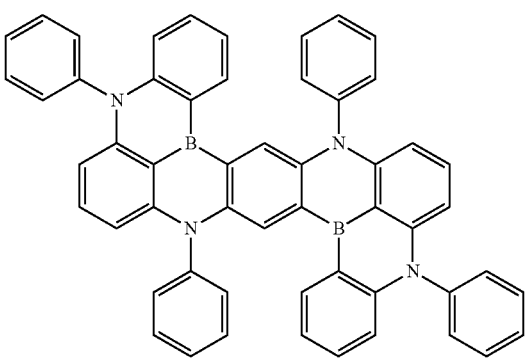
D20
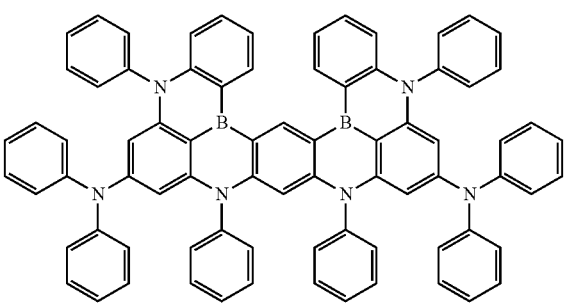
D21
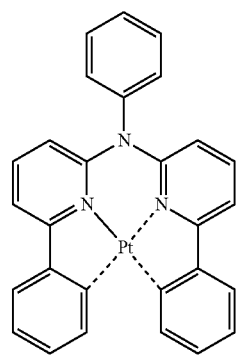

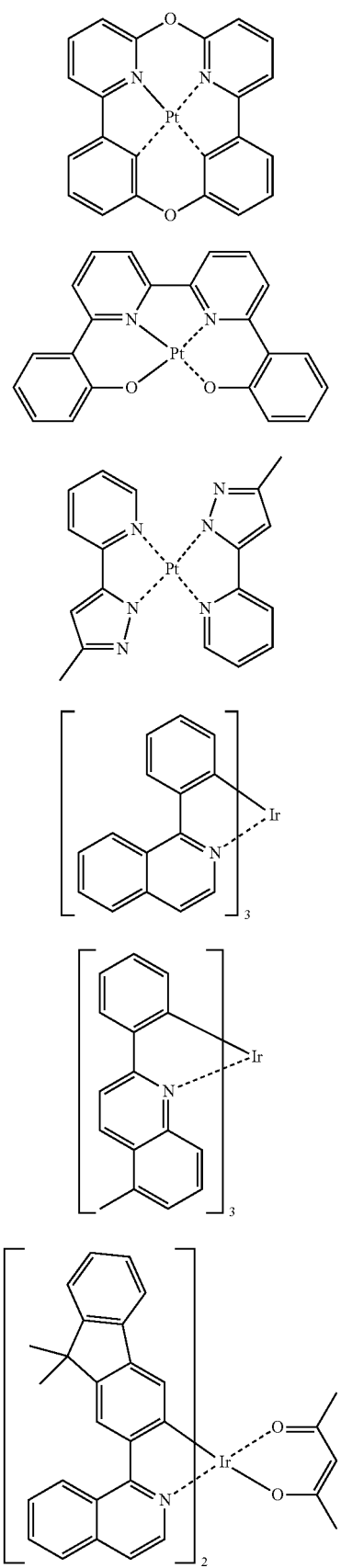

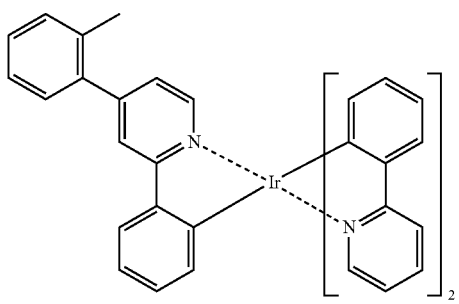

D33

In the organic electroluminescence devices 10 of embodiments, as shown in FIG. 1 to FIG. 4, electron transport regions ETR, ETR-1, and ETR-2 are provided on the emission layers EML, EML-1, and EML-2, respectively.

In the organic electroluminescence device 10 of an embodiment, the electron transport regions ETR, ETR-1, and ETR-2 may include a first compound represented by the following Formula 1:

[Formula 1]

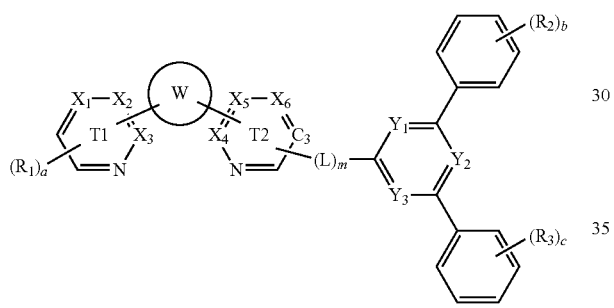

In Formula 1, $X_1$ to $X_6$ may each independently be N or $CR_4$. For example, $X_1$ to $X_6$ all may include carbon atoms.

W may be 0 or 1. If W is 0, then $X_3$ and $X_4$ may make a direct linkage. If W is 1, then W may be a substituted or unsubstituted hydrocarbon ring group of 4 to 60 ring-forming carbon atoms, or a substituted or unsubstituted heterocyclic group of 1 to 60 ring-forming carbon atoms, and W may be combined with ring T1 and ring T2 to form a polycyclic ring.

The T1 ring group may be a ring group including $X_1$ to $X_3$, and the T2 ring group may be a ring group including $X_4$ to $X_6$.

Substituent $C_3$ may be C or CH.

If W, T1, and T2 are combined to form a phenanthroline group, then L may be bonded to $C_3$. $C_3$ may be a carbon atom bonded to L when W, T1, and T2 are combined to form the phenanthroline group. For example, if W is a benzene ring, and W is combined with the T1 ring group including $X_1$ to $X_3$ and the T2 ring group including $X_4$ to $X_6$ to form a polycyclic group, then L may be bonded to $C_3$.

In Formula 1, m may be an integer from 0 to 3. L may be a substituted or unsubstituted hydrocarbon ring group of 4 to 60 ring-forming carbon atoms, or a substituted or unsubstituted heterocyclic group of 1 to 60 ring-forming carbon atoms. If m is an integer greater than 1, then each L groups may be the same or different from each other. For example, if m is 2, then the two L groups may be different as a phenyl group and a naphthyl group, respectively.

In Formula 1, at least one of $Y_1$ to $Y_3$ may be N, and the remainder of $Y_1$ to $Y_3$ may be each independently N or $CR_5$. For example, a ring group including $Y_1$ to $Y_3$ may include at least one nitrogen atom. For example, $Y_1$ and $Y_2$ may be nitrogen atoms, and $Y_3$ may be $CR_5$. In an embodiment, $Y_1$ to $Y_3$ may be all nitrogen atoms.

In Formula 1, a may be 1 or 2, and b and c may each independently be an integer from 1 to 5. If a is 2, then two $R_1$ groups may be the same or different from each other. If b is an integer of 2 or more, then two or more $R_2$ groups may be the same or different from each other. If c is an integer of 2 or more, then two or more $R_3$ groups may be the same or different from each other. For example, if a is 1, then $R_1$ may be a substituted or unsubstituted phenyl group or a cyano group. If b and c are each 5, then the $R_2$ group and $R_3$ groups may be hydrogen atoms. However, an embodiment of the inventive concept is not limited thereto.

$R_1$ to $R_5$ may each independently be a hydrogen atom, a deuterium atom, a substituted or unsubstituted alkoxy group, a substituted or unsubstituted alkyl group of 1 to 60 carbon atoms, a substituted or unsubstituted alkenyl group of 2 to 60 carbon atoms, a substituted or unsubstituted alkynyl group of 2 to 60 carbon atoms, a substituted or unsubstituted aryl group of 6 to 60 ring-forming carbon atoms, or a substituted or unsubstituted heteroaryl group of 1 to 60 ring-forming carbon atoms, or may be combined with an adjacent group to form a ring.

In Formula 1, $X_3$ and $X_4$ may make a direct linkage, and if $X_1$, $X_2$, $X_5$, and $X_6$ are all CH, then $R_1$ is not a hydrogen atom.

According to an embodiment, $R_1$ may be a group represented by one of $R_{1-1}$ to $R_{1-4}$:

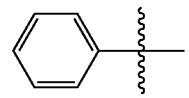

$R_{1-1}$

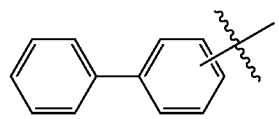

$R_{1-2}$

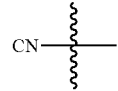

$R_{1-3}$

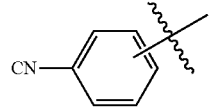

$R_{1-4}$

In an embodiment, Formula 1 may be represented by one of the following Formula 1-1 to Formula 1-3:

[Formula 1-1]

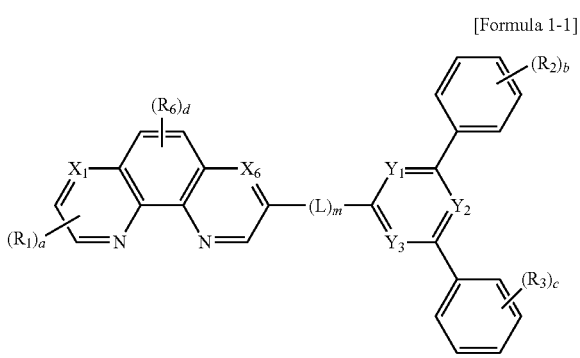

[Formula 1-2]

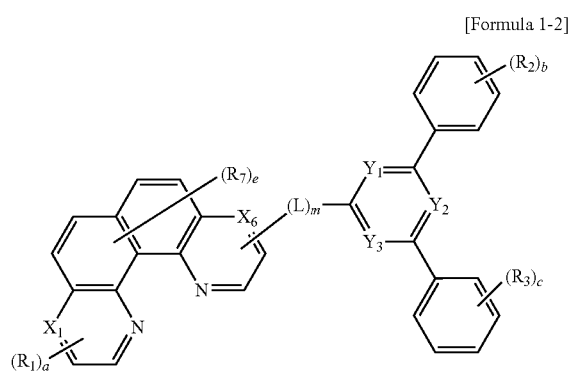

[Formula 1-3]

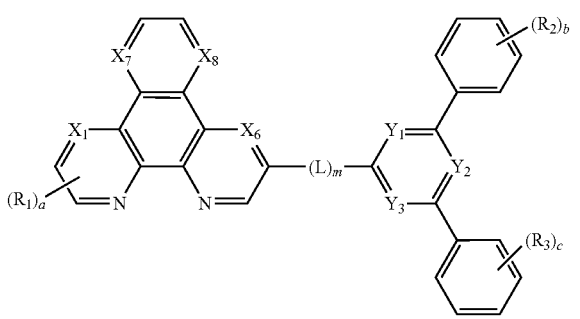

Formula 1-1 to Formula 1-3 represent embodiments where W is 1. Formula 1-1 represents an embodiment where W is a substituted or unsubstituted benzene ring and combined with a T1 ring group including $X_1$ and a T2 ring group including $X_6$ to form a tricyclic group. In Formula 1-1, W, T1, and T2 are combined to form a phenanthroline group. As described above, if W, T1, and T2 are combined to form a phenanthroline group, then L may be bonded to $C_3$.

Formula 1-2 represents an embodiment where W is a substituted or unsubstituted naphthyl group, and W, a T1 ring group including $X_1$ and a T2 ring group including $X_6$ are combined to form a tetracyclic group. Formula 1-3 represents an embodiment where W is a substituted or unsubstituted heteroaryl group of 10 ring-forming carbon atoms, and W, a T1 ring group including $X_1$, and a T2 ring group including $X_6$ are combined to form a tetracyclic group.

The same explanation on a to c, L, m, $R_1$ to $R_3$, $X_1$, $X_6$, and $Y_1$ to $Y_3$ in reference to Formula 1 may be applied to Formula 1-1 to Formula 1-3.

In Formula 1-1, d may be 1 or 2. In Formula 1-2, e may be an integer from 1 to 4. In Formula 1-3, $X_7$ and $X_8$ may each independently be N or $CR_8$. For example, $X_1$, $X_6$, $X_7$ and $X_8$ may be all nitrogen atoms. In an embodiment, $X_1$, $X_6$, $X_7$ and $X_8$ may all include carbon atoms. However, an embodiment of the inventive concept is not limited thereto.

In Formula 1-1 to Formula 1-3, $R_6$ to $R_8$ may each independently be a hydrogen atom, a deuterium atom, a substituted or unsubstituted alkoxy group, a substituted or unsubstituted alkyl group of 1 to 60 carbon atoms, a substituted or unsubstituted alkenyl group of 2 to 60 carbon atoms, a substituted or unsubstituted alkynyl group of 2 to 60 carbon atoms, a substituted or unsubstituted aryl group of 6 to 60 ring-forming carbon atoms, or a substituted or unsubstituted heterocyclic group of 1 to 60 ring-forming carbon atoms.

In an embodiment, Formula 1 may be represented by the following Formula 1-4:

[Formula 1-4]

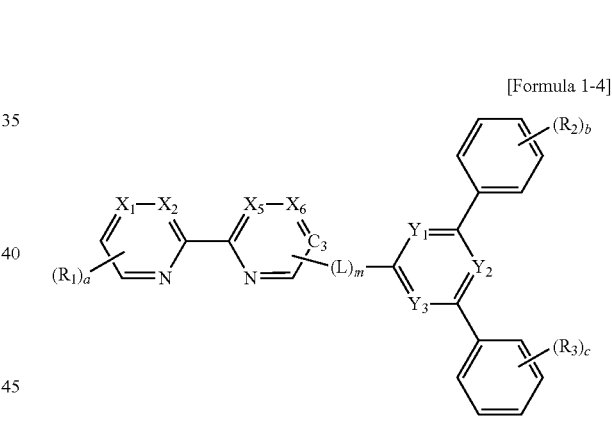

Formula 1-4 represents an embodiment where W is 0, and $X_3$ and $X_4$ are connected via a direct linkage. The same explanation on a to c, L, m, $R_1$ to $R_3$, $X_1$, $X_2$, $X_5$, $X_6$, $C_3$, and $Y_1$ to $Y_3$ in reference to Formula 1 may be applied to Formula 1-4.

In an embodiment, in Formula 1-4, $X_1$, $X_2$, $X_5$, and $X_6$ may be all CH. In another embodiment, in Formula 1-4, $X_1$ and $X_6$ may be CH, and $X_2$ and $X_5$ may be nitrogen atoms. In Formula 1-4, if $X_1$, $X_2$, $X_5$, and $X_6$ are all CH, then $R_1$ is not a hydrogen atom. For example, in Formula 1-4, if $X_1$, $X_2$, $X_5$, and $X_6$ are all CH, then $R_1$ may be a phenyl group. However, an embodiment of the inventive concept is not limited thereto.

In an embodiment, Formula 1 may be represented by one of the following Formula 1-A to Formula 1-D:

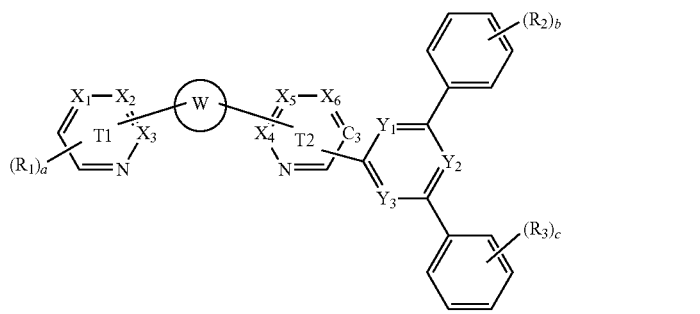
[Formula 1-A]

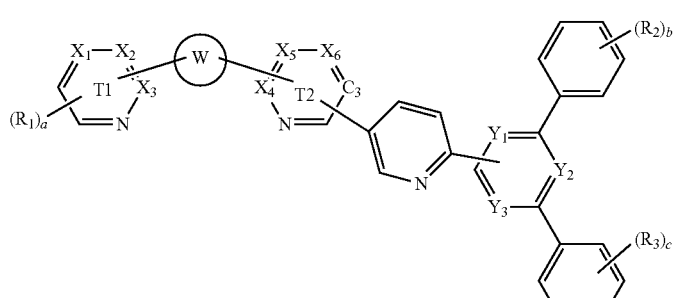
[Formula 1-B]

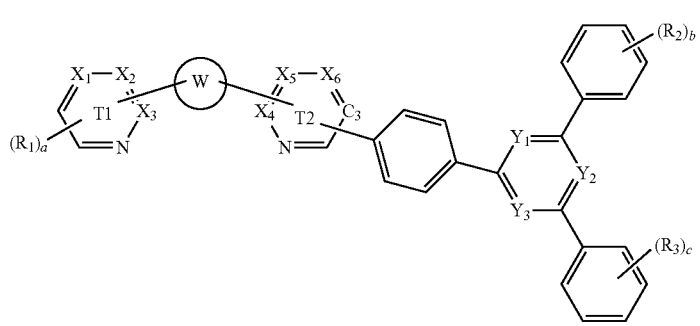
[Formula 1-C]

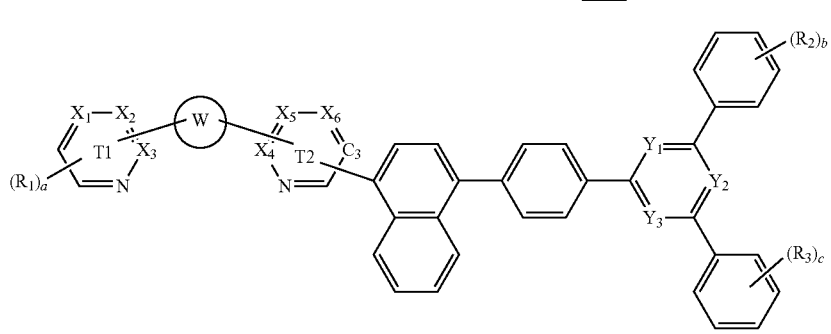
[Formula 1-D]

Formula 1-A represents an embodiment where m is 0, and a ring group including $Y_1$ to $Y_3$ makes a direct linkage with ring T2. Formula 1-B and Formula 1-C represent embodiments where m is 1. Formula 1-D represents an embodiment where m is 2.

Formula 1-B represents an embodiment where L is a pyridylene group. Formula 1-C represents an embodiment where L is a phenylene group. Formula 1-D represents a an embodiment where the L groups include a naphthalene group and a phenylene group.

The same explanation on a to c, $R_1$ to $R_3$, W, T1, T2, $X_1$ to $X_6$, $C_3$, and $Y_1$ to $Y_3$ in reference to Formula 1 may be applied to Formula 1-A to Formula 1-D.

Formula 1-A may be represented by the following Formula 1-AA, Formula 1-B may be represented by the following Formula 1-BB, Formula 1-C may be represented by the following Formula 1-CC, and Formula 1-D may be represented by the following Formula 1-DD:

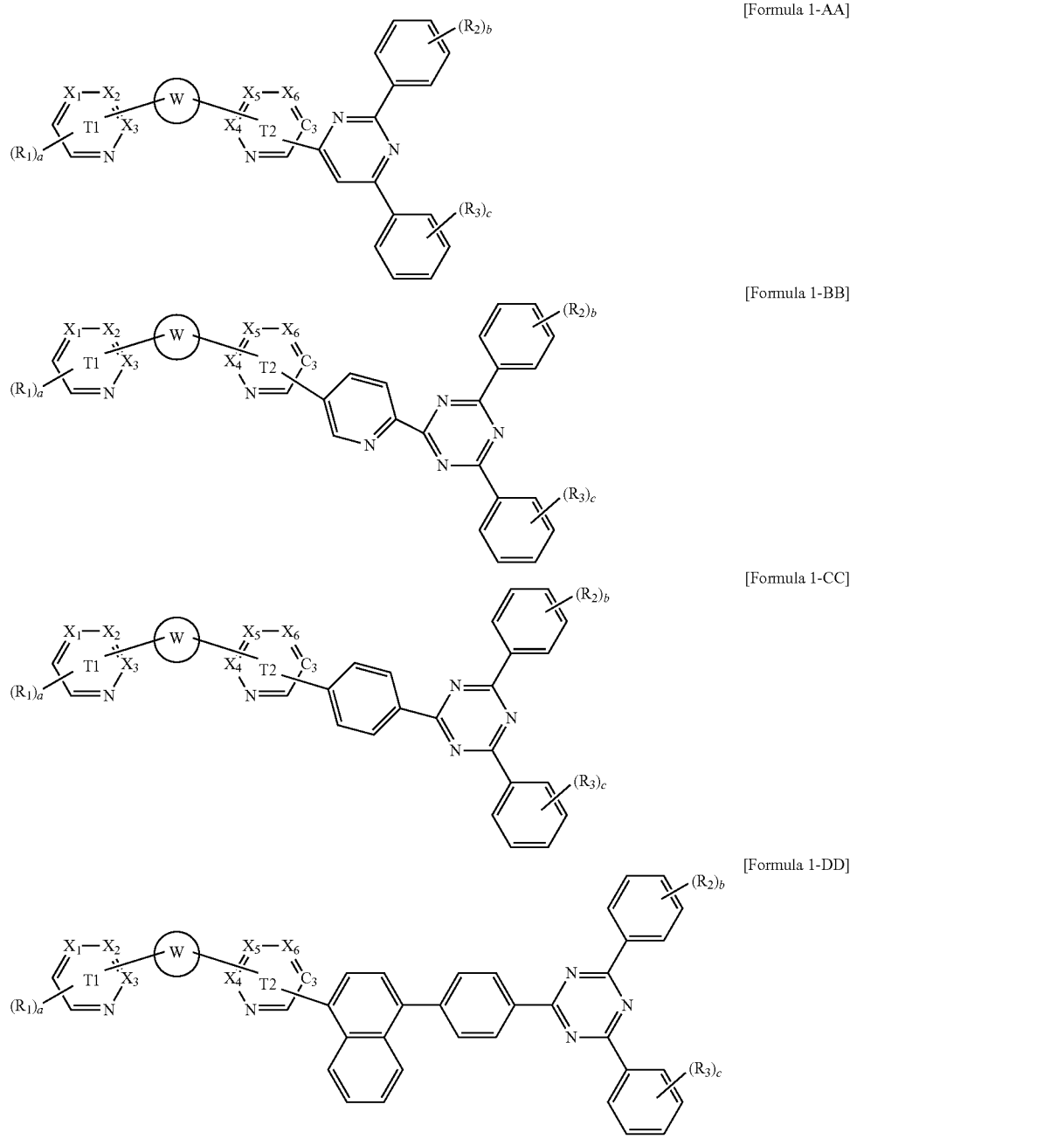

[Formula 1-AA]

[Formula 1-BB]

[Formula 1-CC]

[Formula 1-DD]

Formula 1-AA represents an embodiment where two of $Y_1$ to $Y_3$ are nitrogen atoms, and a ring group including $Y_1$ to $Y_3$ makes a direct linkage with ring T2. Formula 1-BB represents an embodiment where $Y_1$ to $Y_3$ are all nitrogen atoms, and L is a pyridylene group. Formula 1-CC represents an embodiment where $Y_1$ to $Y_3$ are all nitrogen atoms, and L is a phenylene group. Formula 1-DD represents an embodiment where $Y_1$ to $Y_3$ are all nitrogen atoms, and L is a naphthalene group with a phenylene group.

The same explanation on a to c, $R_1$ to $R_3$, W, T1, T1, $C_3$, and $X_1$ to $X_6$ in reference to Formula 1 may be applied to Formula 1-AA to Formula 1-DD.

The first compound of an embodiment includes two or more heterocyclic groups including at least one nitrogen atom and may control the moving speed of electrons, and accordingly, may contribute to the improvement of the emission efficiency of an organic electroluminescence device.

The first compound of an embodiment represented by Formula 1 may be one selected from Compound Group 1, which includes Compounds 1-1 to 1-12. For example, the organic electroluminescence device 10 of an embodiment may include at least one of the first compounds represented in the following Compound Group 1 in electron transport regions ETR, ETR-1, and ETR-2:

[Compound Group 1]
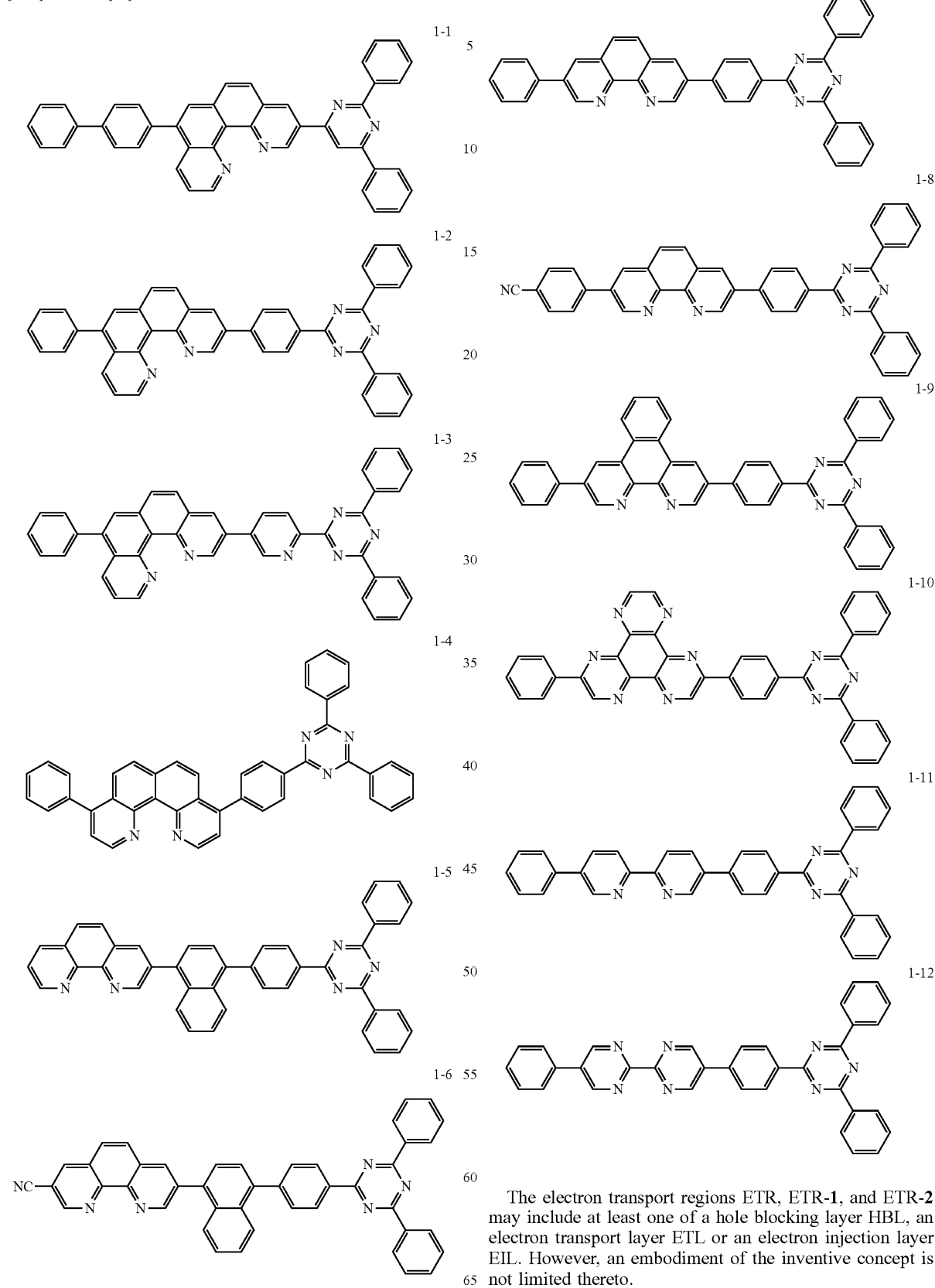
The electron transport regions ETR, ETR-1, and ETR-2 may include at least one of a hole blocking layer HBL, an electron transport layer ETL or an electron injection layer EIL. However, an embodiment of the inventive concept is not limited thereto.
The electron transport regions ETR, ETR-1, and ETR-2 may have a single layer formed using a single material, a single layer formed using different materials, or a multilayer structure having multiple layers formed using different materials.

For example, the electron transport regions ETR, ETR-1, and ETR-2 may have a single layer structure of an electron injection layer EIL or an electron transport layer ETL, or a single layer structure formed using an electron injection material and an electron transport material. The electron transport regions ETR, ETR-1, and ETR-2 may have a single layer structure having different materials, or a structure stacked from the emission layers EML, ETR-1, and ETR-2 of electron transport layer ETL/electron injection layer EIL, or hole blocking layer HBL/electron transport layer ETL/electron injection layer EIL, without limitation. The thickness of each of the electron transport regions ETR, ETR-1, and ETR-2 may be in a range of about 300 Å to about 1,500 Å.

The electron transport regions ETR, ETR-1, and ETR-2 may be formed using various methods such as a vacuum deposition method, a spin coating method, a cast method, a Langmuir-Blodgett (LB) method, an inkjet printing method, a laser printing method, and a laser induced thermal imaging (LITI) method.

The electron transport regions ETR, ETR-1, and ETR-2 may further include a known material in addition to the first compound represented by Formula 1. If the electron transport regions ETR, ETR-1, and ETR-2 include an electron transport layer ETL, the electron transport regions ETR, ETR-1, and ETR-2 may include an anthracene-based compound. The electron transport regions ETR, ETR-1, and ETR-2 may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-yl)phenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP),4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate ($Bebq_2$), 9,10-di(naphthalene-2-yl)anthracene (ADN), 1,3-bis [3,5-di(pyridine-3-yl)phenyl]benzene (BmPyPhB), or mixtures thereof. The thickness of the electron transport layer ETL may be in a range of about 100 Å to about 1,000 Å. For example, the thickness of the electron transport layer ETL may be in a range of about 150 Å to about 500 Å. If the thickness of the electron transport layer ETL satisfies the above-described range, satisfactory electron transport properties may be obtained without substantial increase of a driving voltage.

If the electron transport region ETR includes the electron injection layer EIL, the electron transport region ETR may include, a metal halide such as LiF, NaCl, CsF, RbCl and RbI, a lanthanide metal such as Yb, a metal oxide such as $Li_2O$ and BaO, or lithium quinolate (Liq). However, an embodiment of the inventive concept is not limited thereto. The electron injection layer EIL may be also formed using a mixture material of an electron transport material and an insulating organo metal salt. The organo metal salt may be a material having an energy band gap of about 4 eV or more. The organo metal salt may include, for example, metal acetates, metal benzoates, metal acetoacetates, metal acetylacetonates, or metal stearates. The thickness of the electron injection layer EIL may be in a range of about 1 Å to about 100 Å. For example, the thickness of the electron injection layer EIL may be in a range of about 3 Å to about 90 Å. If the thickness of the electron injection layer EIL satisfies the above described range, satisfactory electron injection properties may be obtained without inducing substantial increase of a driving voltage.

The electron transport region ETR may include a hole blocking layer HBL as described above. The hole blocking layer HBL may include, for example, at least one of 2,9-dimethyl-4,7-diphenyl-1,10-phenanthroline (BCP), or 4,7-diphenyl-1,10-phenanthroline (Bphen). However, an embodiment of the inventive concept is not limited thereto.

The second electrode EL2 is provided on the electron transport region ETR. The second electrode EL2 may be a common electrode or a cathode. The second electrode EL2 may be a transmissive electrode, a transflective electrode, or a reflective electrode. If the second electrode EL2 is a transmissive electrode, the second electrode EL2 may include a transparent metal oxide, for example, ITO, IZO, ZnO, ITZO, etc.

If the second electrode EL2 is a transflective electrode or a reflective electrode, the second electrode EL2 may include Ag, Mg, Cu, Al, Pt, Pd, Au, Ni, Nd, Jr, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer or a transflective layer formed using the above-described materials and a transparent conductive layer formed using ITO, IZO, ZnO, ITZO, etc.

Though not shown, the second electrode EL2 may be electrically connected with an auxiliary electrode. If the second electrode EL2 is electrically connected with the auxiliary electrode, the resistance of the second electrode EL2 may decrease.

On the second electrode EL2 of the organic electroluminescence device 10 of an embodiment, a capping layer (CPL) may be further disposed. The capping layer (CPL) may include, for example, α-NPD, NPB, TPD, m-MTDATA, $Alq_3$, CuPc, N4,N4,N4',N4'-tetra(biphenyl-4-yl) biphenyl-4,4'-diamine (TPD15), 4,4',4"-tris(carbazol sol-9-yl) triphenylamine (TCTA), N,N'-bis(naphthalene-1-yl), etc. However, an embodiment of the inventive concept is not limited thereto, and the capping layer may be omitted from the organic electroluminescence device.

In FIG. 4, in contrast to FIG. 1 to FIG. 3, an organic electroluminescence device 10 including hole transport regions HTR-1 and HTR-2, emission layers EML-1 and EML-2, and electron transport regions ETR-1 and ETR-2 is shown. With respect to the hole transport regions HTR-1 and HTR-2, the emission layers EML-1 and EML-2, and the electron transport regions ETR-1 and ETR-2, the same explanation referring to the aforementioned hole transport region, emission layer, and electron transport region may be applied, respectively.

The organic electroluminescence device 10 of an embodiment may include light-emitting units LU-1 and LU-2. Each of the light-emitting units LU-1 and LU-2 may include a hole transport region, an emission layer disposed on the hole transport region, and an electron transport region disposed on the emission layer. Referring to FIG. 4, the first light-emitting unit LU-1 may include a first hole transport region HTR-1, a first emission layer EML-1, and a first electron transport region ETR-1, and the second light-emitting unit LU-2 may include a second hole transport region HTR-2, a second emission layer EML-2, and a second electron transport region ETR-2. However, an embodiment of the inventive concept is not limited thereto, and the organic electroluminescence device may include three or more light-emitting units.

According to an embodiment, at least one charge generating layer CGL may be disposed between adjacent light-emitting units LU-1 and LU-2. For example, an organic electroluminescence device including three light-emitting units may include two charge generating layers. The charge generating layer CGL may include the first compound of an embodiment.

The charge generating layer CGL is a layer which is capable of generating an electron-hole pair, and holes generated from the charge generating layer CGL may be transferred to one light-emitting unit, and electrons may be transferred to the other light-emitting unit. For example, if a first electrode EL1 is an anode, and a second electrode EL2 is a cathode, electrons generated from the charge generating layer CGL may move to a first light-emitting unit LU-1 and form excitons with holes injected from the first electrode EL1, and holes may move to a second light-emitting unit LU-2 and form excitons with electrons injected from the second electrode EL2.

The first hole transport region HTR-1 and the second hole transport region HTR-2 may include the same material or different materials. For example, the first hole transport region HTR-1 or the second hole transport region HTR-2 may include the aforementioned second compound of an embodiment and may further include a known material. Otherwise, the first hole transport region HTR-1 and the second hole transport region HTR-2 all may include the second compound. The first hole transport region HTR-1 and the second hole transport region HTR-2 all may include the second compound, and at least one of the first hole transport region HTR-1 or the second hole transport region HTR-2 may further include a known material. The first hole transport region HTR-1 and the second hole transport region HTR-2 all may include the second compound, and the first hole transport region HTR-1 and the second hole transport region HTR-2 all may further include a known material.

The first electron transport region ETR-1 and the second electron transport region ETR-2 may include the same material or different materials from each other. For example, the first electron transport region ETR-1 and the second electron transport region ETR-2 may include the aforementioned first compound of an embodiment, and the first electron transport region ETR-1 and the second electron transport region ETR-2 all may further include a known material. The first electron transport region ETR-1 may include the first compound of an embodiment, and the second electron transport region ETR-2 may include a known material. The first electron transport region ETR-1 may include the first compound of an embodiment, and the first electron transport region ETR-1 and the second electron transport region ETR-2 all may further include a known material. The second electron transport region ETR-2 may include the first compound of an embodiment, and the first electron transport region ETR-1 and the second electron transport region ETR-2 all may further include a known material.

The first emission layer EML-1 and the second emission layer EML-2 may emit different colors from each other. For example, the first emission layer EML-1 may emit blue light, and the second emission layer EML-2 may emit red light and green light. Differently, the first emission layer EML-1 and the second emission layer EML-2 may emit the same color light. However, an embodiment of the inventive concept is not limited thereto.

For example, if the organic electroluminescence device of an embodiment includes three light-emitting units, three emission layers may emit the same color, or three emission layers may emit different colors, respectively. If three emission layers emit different colors, the organic electroluminescence device may emit white light. In an embodiment, in the organic electroluminescence device, two emission layers may emit the same color light, and one emission layer may emit different color light. However, these are only illustrations, and an embodiment of the inventive concept is not limited to any one thereof.

The organic electroluminescence device according to an embodiment may include the first compound of an embodiment in an electron transport region, and may show a reduced driving voltage and improved emission efficiency. The organic electroluminescence device of an embodiment, including light-emitting units may include the first compound of an embodiment in a charge generating layer and an electron transport region, and may show improved emission efficiency.

Hereinafter, the compound according to an embodiment and the organic electroluminescence device of an embodiment of the inventive concept will be explained referring to embodiments and comparative embodiments. The following embodiments are only illustrations to assist the understanding of the inventive concept, and the scope of the inventive concept is not limited thereto.

EXAMPLES

1. Synthesis of First Compound and Second Compound

First, the synthetic method of the first compound and the second compound according to an embodiment will be explained in detail referring to the synthetic methods of Compound 1-5 and Compound 1-8 in Compound Group 1, and Compound 2-1 and Compound 2-4 in Compound Group 2. The synthetic methods of the first compound and the second compound explained below are only embodiments, and the synthetic method of the first compound and the second compound according to an embodiment of the inventive concept is not limited thereto.

<Synthesis of Compound 1-5>

Compound 1-5 according to an embodiment may be synthesized by, for example, the steps of the following Reaction 1:

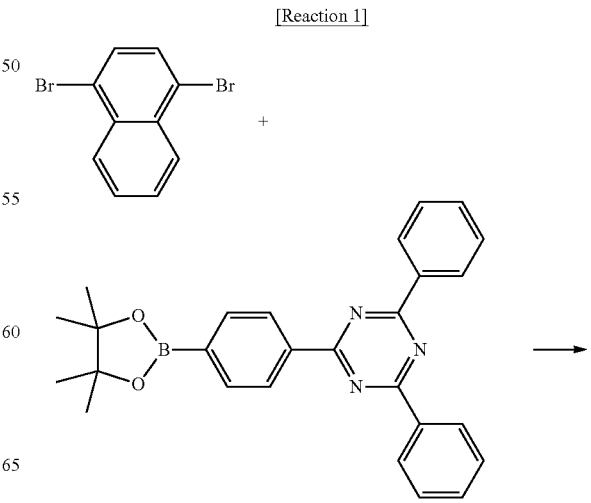

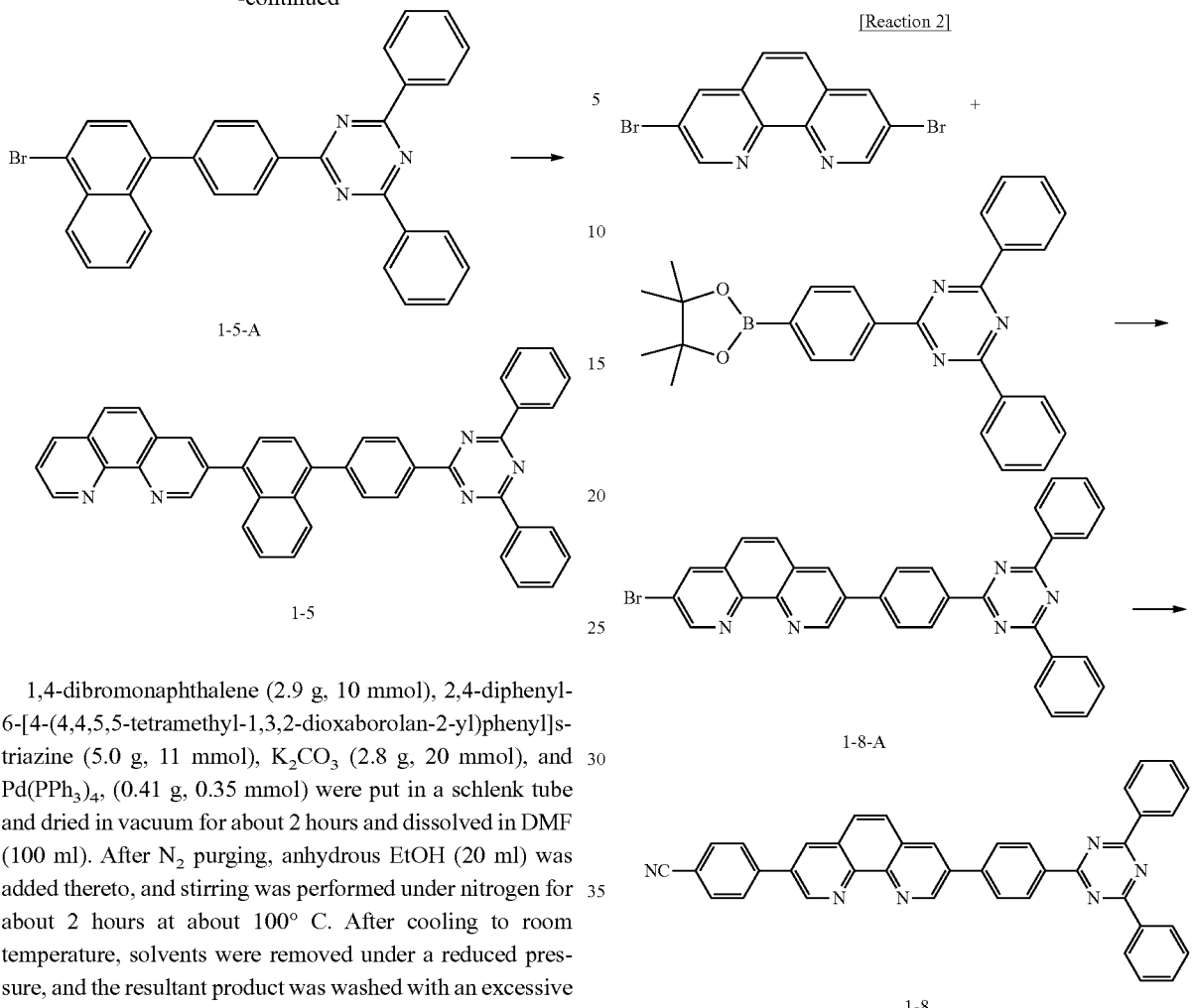

1,4-dibromonaphthalene (2.9 g, 10 mmol), 2,4-diphenyl-6-[4-(4,4,5,5-tetramethyl-1,3,2-dioxaborolan-2-yl)phenyl]-s-triazine (5.0 g, 11 mmol), K$_2$CO$_3$ (2.8 g, 20 mmol), and Pd(PPh$_3$)$_4$, (0.41 g, 0.35 mmol) were put in a schlenk tube and dried in vacuum for about 2 hours and dissolved in DMF (100 ml). After N$_2$ purging, anhydrous EtOH (20 ml) was added thereto, and stirring was performed under nitrogen for about 2 hours at about 100° C. After cooling to room temperature, solvents were removed under a reduced pressure, and the resultant product was washed with an excessive amount of DCM and distilled water. An organic layer was separated, and the separated organic layer was dried with MgSO$_4$. The crude product thus obtained was separated by column chromatography (dichloromethane/hexane, 2:1, v/v) to obtain 1-5-A (3.5 g, 6.8 mmol, yield 68%).

1-5-A (5.1 g, 10 mmol), (1,10-phenanthrolin-3-yl)boronic acid (2.6 g, 12 mmol), K$_2$CO$_3$ (2.8 g, 20 mmol), and Pd(PPh$_3$)$_4$ (0.41 g, 0.35 mmol) were put in a schlenk tube and dried in vacuum for about 2 hours and dissolved in DMF (100 ml). After N$_2$ purging, anhydrous EtOH (20 ml) was added thereto, and stirring was performed under nitrogen for about 48 hours at about 100° C. After cooling to room temperature, solvents were removed under a reduced pressure, and the resultant product was washed with an excessive amount of chloroform and distilled water. An organic layer was separated, and the separated organic layer was dried with MgSO$_4$. The crude product thus obtained was separated by column chromatography (using chloroform) to obtain Compound 1-5 (3.1 g, 5.1 mmol, yield 51%). $^1$NMR (d$^6$-DMSO, 500 MHz): δ 7.25 (2H), 7.46-7.56 (9H), 7.84 (1H), 7.91 (1H), 7.96 (2H), 8.06 (1H), 8.12 (2H), 8.20 (1H), 8.26 (1H), 8.36 (4H), 8.45 (1H), 8.80 (1H), 8.95-9.01 (2H) ppm.

<Synthesis of Compound 1-8>

Compound 1-8 according to an embodiment may be synthesized by, for example, the steps of the following Reaction 2:

3,8-dibromo-1,10-phenanthroline (3.4 g, 10 mmol), 2,4-diphenyl-6-[4-(4,4,5,5-tetramethyl-1,3,2-dioxaborolan-2-yl)phenyl]-s-triazine (5.0 g, 11 mmol), K$_2$CO$_3$ (2.8 g, 20 mmol), and Pd(PPh$_3$)$_4$ (0.41 g, 0.35 mmol) were put in a schlenk tube and dried in vacuum for about 2 hours and dissolved in DMF (100 ml). After N$_2$ purging, anhydrous EtOH (20 ml) was added thereto, and stirring was performed under nitrogen for about 24 hours at about 100° C. After cooling to room temperature, solvents were removed under a reduced pressure, and the resultant product was washed with an excessive amount of dichloromethane and distilled water. An organic layer was separated, and the separated organic layer was dried with MgSO$_4$. The crude product thus obtained was separated by column chromatography (dichloromethane/hexane, 10:1, v/v) to obtain 1-8-A (4.4 g, 7.7 mmol, yield 77%).

1-8-A (5.7 g, 10 mmol), (4-cyanophenyl)boronic acid (1.8 g, 12 mmol), K$_2$CO$_3$ (1.4 g, 10 mmol), and Pd(PPh$_3$)$_4$ (0.41 g, 0.35 mmol) were put in a schlenk tube and dried in vacuum for about 2 hours and dissolved in 1,4-dioxane (100 ml). After N$_2$ purging, anhydrous EtOH (20 ml) was added thereto, and stifling was performed under nitrogen for about 24 hours at about 80° C. After cooling to room temperature, solvents were removed under a reduced pressure, and the resultant product was washed with an excessive amount of chloroform and distilled water. An organic layer was separated, and the separated organic layer was dried with MgSO$_4$. The crude product thus obtained was separated by column chromatography (chloroform) to obtain Compound 1-8 (3.7 g, 6.3 mmol, yield 63%). $^1$NMR (d$^6$-DMSO, 500 MHz): δ 7.25 (3H), 7.50 (6H), 7.84 (4H), 7.91-7.96 (3H), 8.12 (1H), 8.20-8.26 (4H), 8.36 (4H) ppm.

<Synthesis of Compound 2-1>

Compound 2-1 according to an embodiment may be synthesized by, for example, the steps of the following Reaction 3:

product thus obtained was separated by column chromatography (hexane:dichloromethane, 5:1, v/v). By removing solvents, Compound 2-1 was obtained as a white solid (4.6 g, 6.6 mmol, yield 66%). $^1$NMR (d$^6$-DMSO, 500 MHz): δ 0.88 (6H, —CH$_3$), 1.29 (16H, —CH$_2$—), 1.69 (6H, —CH$_3$), 1.83 (4H, —CH$_2$—), 7.16 (2H), 7.28-7.49 (11H), 7.55 (4H), 7.75 (2H), 7.86 (2H), 7.90 (2H) ppm.

<Synthesis of Compound 2-4>

Compound 2-4 according to an embodiment may be synthesized by, for example, the steps of the following Reaction 4:

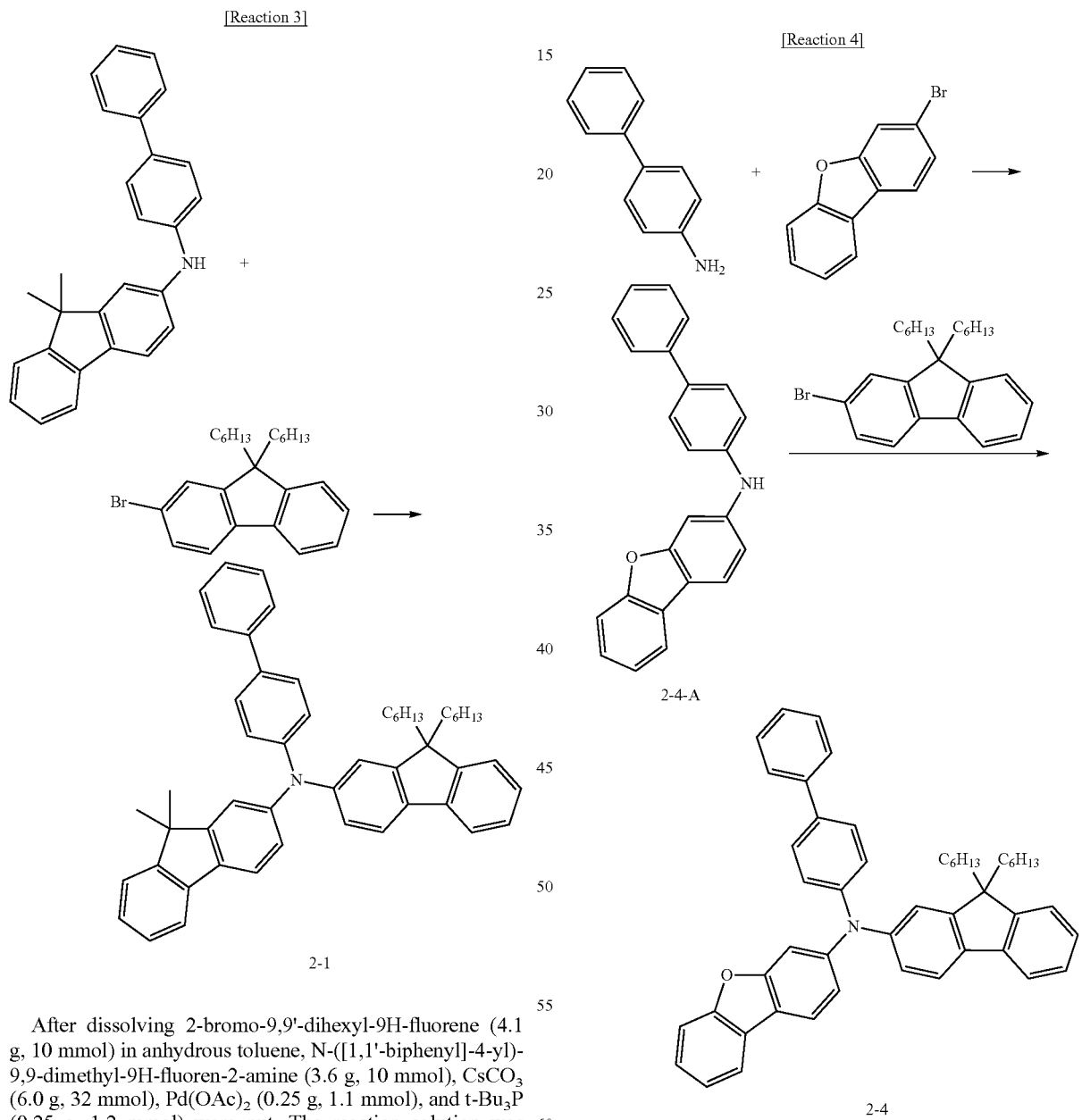

After dissolving 2-bromo-9,9'-dihexyl-9H-fluorene (4.1 g, 10 mmol) in anhydrous toluene, N-([1,1'-biphenyl]-4-yl)-9,9-dimethyl-9H-fluoren-2-amine (3.6 g, 10 mmol), CsCO$_3$ (6.0 g, 32 mmol), Pd(OAc)$_2$ (0.25 g, 1.1 mmol), and t-Bu$_3$P (0.25 g, 1.2 mmol) were put. The reaction solution was stirred under nitrogen at about 120° C. for about 24 hours. After cooling the solution to room temperature, solvents were removed under a reduced pressure, and remaining solid was extracted with dichloromethane. The solution thus extracted was washed with water and a brine solution, and water was removed with MgSO$_4$. The solution thus obtained was filtered to remove solid and concentrated. The crude 4-aminobiphenyl (17 g, 0.10 mol), 3-bromodibenzofuran (25 g, 0.10 mol), t-BuONa (14 g, 0.15 mol), t-Bu$_3$P (0.6 g, 3.0 mmol), and Pd 2 (dba) 3 (2.7 g, 3.0 mmol) were put in a schlenk tube and dried in vacuum for about 2 hours and dissolved in toluene (500 ml). After stirring under nitrogen for about 24 hours at about 130° C., the temperature was reduced to room temperature. Solvents were removed under a reduced pressure, and the resultant product was washed with an excessive amount of dichloromethane and distilled water. An organic layer was separated, and the separated organic layer was dried with MgSO$_4$. The crude product thus obtained was separated by column chromatography (using dichloromethane) to obtain 2-4-A (26 g, 78 mmol, yield 78%).

After dissolving 2-bromo-9,9'-dihexyl-9H-fluorene (4.1 g, 10 mmol) in anhydrous toluene, 2-4-A (3.3 g, 10 mmol), Cs$_2$CO$_3$ (6.0 g, 32 mmol), Pd(OAc)$_2$ (0.25 g, 1.1 mmol), and t-Bu$_3$P (0.25 g, 1.2 mmol) were put. The reaction solution was stirred under nitrogen for about 24 hours at about 130° C. After cooling the solution to room temperature, solvents were removed under a reduced pressure, and the resultant solid was extracted with dichloromethane. The solution thus extracted was washed with water and a brine solution, and water was removed with MgSO$_4$. The solution was filtered to remove solid and concentrated. The crude product thus obtained was separated by column chromatography (hexane:dichloromethane, 1:1, v/v). By removing solvents, Compound 2-4 was obtained as a white solid (4.0 g, 5.9 mmol, yield 59%). $^1$NMR (d$^6$-DMSO, 500 MHz): δ 0.87 (6H, —CH$_3$), 1.26-1.30 (16H, —CH$_2$—), 1.83 (4H, —CH$_2$—), 6.91 (1H), 7.28 (1H), 7.31-7.41 (7H), 7.49-7.55 (6H), 7.75-7.86 (4H), 7.90-7.98 (2H), 8.03 (1H) ppm.

2. Manufacture and Evaluation of Organic Electroluminescence Device Including First Compound and Second Compound (Manufacture of Organic Electroluminescence Device)

An organic electroluminescence device of an embodiment, including the first compound of an embodiment in an electron transport region and the second compound in a hole transport region was manufactured by a method below.

Organic electroluminescence devices of Example 1 to Example 12 were manufactured using Compounds 1-5 and 1-8 as materials of an electron transport layer. The organic electroluminescence devices of Example 5 to Example 12 were manufactured using Compounds 2-1 and 2-4 as materials of a hole transport region. The compounds used for the manufacture of the organic electroluminescence devices of the Comparative Examples and the Examples are shown below.

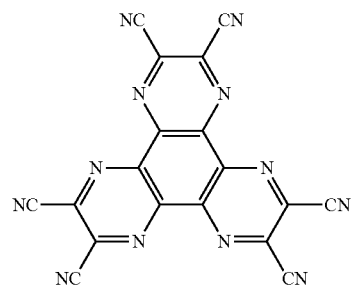

[HAT-CN]

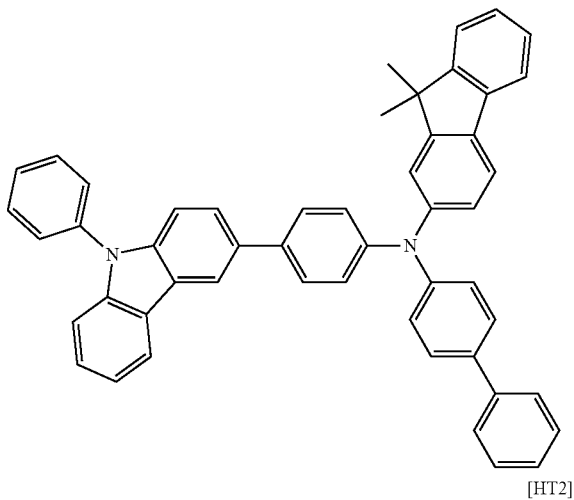

[HT1]

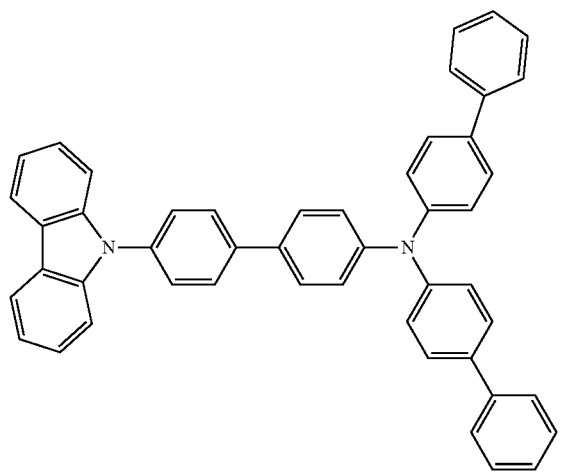

[HT2]

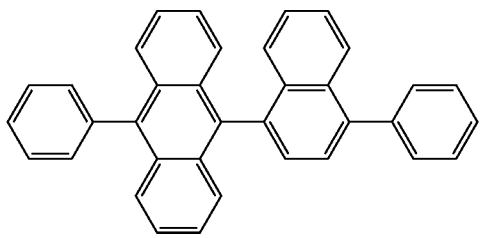

[HOST1]

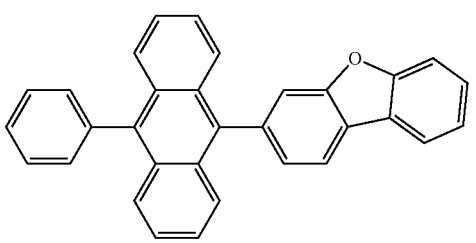

[HOST2]

-continued

[DOPANT1]

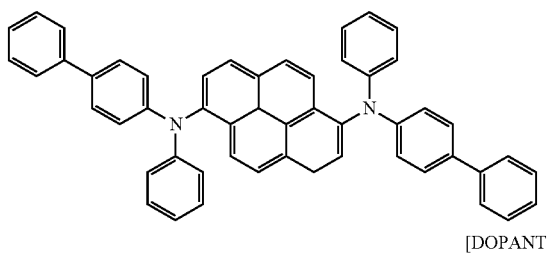

[DOPANT2]

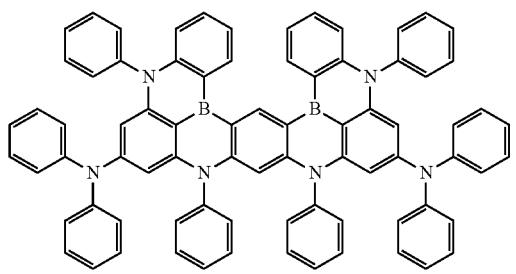

[T2T]

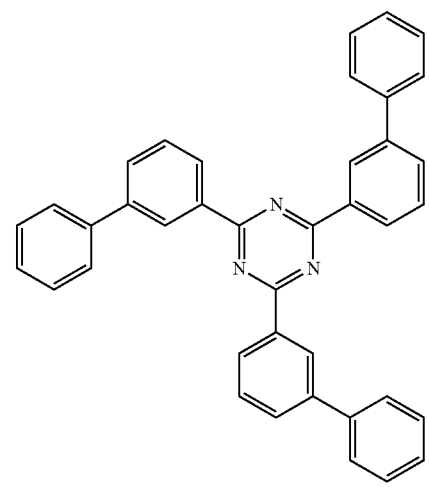

[TPBi]

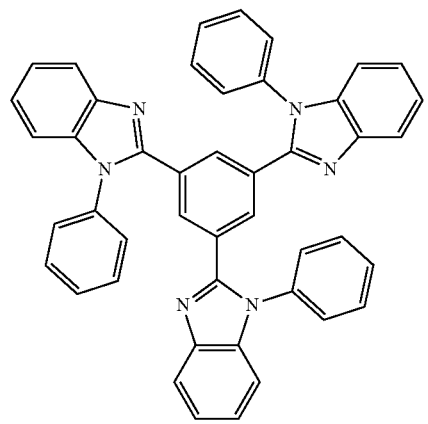

-continued

[ET1]

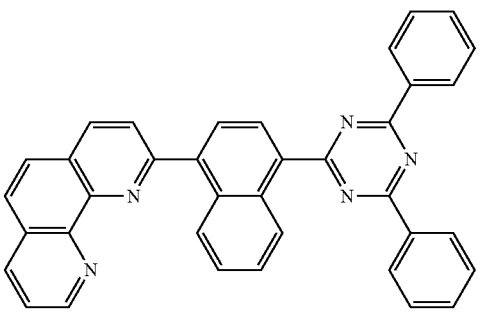

1-5

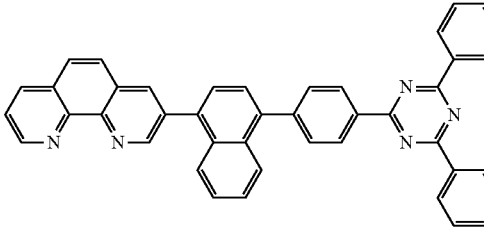

1-8

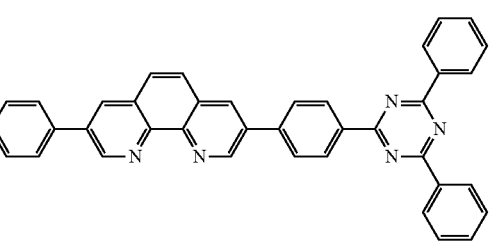

2-1

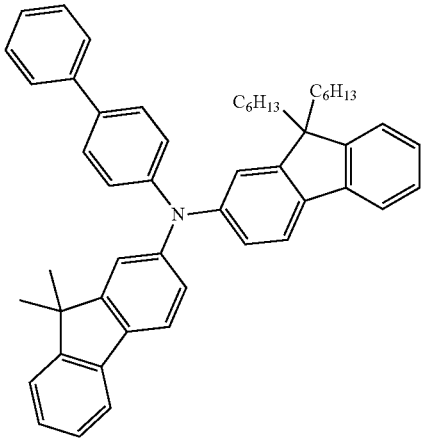

The organic electroluminescence device of Comparative Example 1 was manufactured by a method below. An ITO glass substrate was cut into a size of 50 mm×50 mm×0.5 mm, washed by ultrasonic waves using isopropyl alcohol and pure water for about 10 minutes, respectively, and washed by irradiating ultraviolet rays for about 10 minutes and then ozone. The glass substrate was installed in a vacuum deposition apparatus. HAT-CN was vacuum deposited to a thickness of about 100 Å to form a hole injection layer, and HT1 was vacuum deposited as a first hole transport layer material. On the first hole transport layer, a HT2 material was vacuum deposited to a layer thickness of about 50 Å to form a second hole transport layer (or electron blocking layer). An emission layer was formed by depositing HOST1:DOPANT1 in a ratio of 97:3 wt % to a thickness of about 300 Å. On the emission layer, T2T was vacuum deposited to a thickness of about 50 Å to form a hole blocking layer. TPBi and lithium quinolate (LiQ) were vacuum deposited in a ratio of 1:1 wt % to a thickness of about 300 Å to form an electron transport layer. As an electron injection layer and a cathode, LiF and Al were deposited to about 8 Å and about 1,000 Å, respectively.

The organic electroluminescence device of Comparative Example 2 was manufactured by a method below. An ITO glass substrate was cut into a size of 50 mm×50 mm×0.5 mm, washed by ultrasonic waves using isopropyl alcohol and pure water for about 10 minutes, respectively, and washed by irradiating ultraviolet rays for about 10 minutes and then ozone. The glass substrate was installed in a vacuum deposition apparatus. HAT-CN was vacuum deposited to a thickness of about 100 Å to form a hole injection layer, and HT1 was vacuum deposited as a first hole transport layer material. On the first hole transport layer, a HT2 material was vacuum deposited to a layer thickness of about 50 Å to form a second hole transport layer (or electron blocking layer). An emission layer was formed by depositing HOST2:DOPANT2 in a ratio of 97:3 wt % to a thickness of about 300 Å. On the emission layer, T2T was vacuum deposited to a thickness of about 50 Å to form a hole blocking layer. TPBi and lithium quinolate (LiQ) were vacuum deposited in a ratio of 1:1 wt % to a thickness of about 300 Å to form an electron transport layer. As an electron injection layer and a cathode, LiF and Al were deposited to about 8 Å and about 1,000 Å, respectively.

The organic electroluminescence devices of Comparative Example 3 and Comparative Example 4 were manufactured by the same method for manufacturing the organic electroluminescence devices of Comparative Example 1 and Comparative Example 2 except for using ET1 as an electron transport layer material.

The organic electroluminescence devices of Example 1 to Example 12 were manufactured using Compound 2-1 as a material for a hole injection layer or a hole transport layer, and using Compound 1-5 or Compound 1-8 as a material for an electron transport layer. In the case of using Compound 2-1 as the material for a hole injection layer or a hole transport layer, 1 wt % of NDP-9 (Novaled) was co-deposited.

(Evaluation of Properties of Organic Electroluminescence Device)

The evaluation results of the organic electroluminescence devices of Example 1 to Example 12, Comparative Example 1, and Comparative Example 2 are shown in Table 1. The driving voltage, emission efficiency and device life of the organic electroluminescence devices thus manufactured are shown in Table 1. In the evaluation results on the properties of the Examples and the Comparative Examples in Table 1, the emission efficiency represents an efficiency value at a current density corresponding to a luminance of 1000 nit, and the device life T95 represents time required for reducing initial brightness by 5%.

TABLE 1

| Division | HIL | HTL-1 | HTL-2 | Host | Dopant | Electron transport layer | EQE (%) | Driving voltage (V) | Life T95 (h) |
|---|---|---|---|---|---|---|---|---|---|
| Comparative Example 1 | HAT-CN | HT1 | HT2 | HOST1 | DOPANT1 | TPBi | 5.4 | 4.3 | 45 |
| Comparative Example 2 | HAT-CN | HT1 | HT2 | HOST2 | DOPANT2 | TPBi | 6.1 | 4.0 | 81 |
| Comparative Example 3 | HAT-CN | HT1 | HT2 | HOST1 | DOPANT1 | ET1 | 5.7 | 4.3 | 42 |
| Comparative Example 4 | HAT-CN | HT1 | HT2 | HOST2 | DOPANT2 | ET1 | 6.5 | 4.1 | 78 |
| Example 1 | HAT-CN | HT1 | HT2 | HOST1 | DOPANT1 | 1-5 | 7.2 | 4.3 | 56 |
| Example 2 | HAT-CN | HT1 | HT2 | HOST2 | DOPANT2 | 1-5 | 7.9 | 4.0 | 101 |
| Example 3 | HAT-CN | HT1 | HT2 | HOST1 | DOPANT1 | 1-8 | 8.9 | 4.0 | 75 |
| Example 4 | HAT-CN | HT1 | HT2 | HOST2 | DOPANT2 | 1-8 | 9.6 | 3.9 | 142 |
| Example 5 | 2-1 | HT1 | HT2 | HOST1 | DOPANT1 | 1-5 | 8.2 | 3.9 | 68 |
| Example 6 | 2-1 | HT1 | HT2 | HOST2 | DOPANT2 | 1-5 | 9.0 | 3.7 | 123 |
| Example 7 | 2-1 | HT1 | HT2 | HOST1 | DOPANT1 | 1-8 | 9.5 | 3.8 | 80 |
| Example 8 | 2-1 | HT1 | HT2 | HOST2 | DOPANT2 | 1-8 | 9.8 | 3.6 | 147 |
| Example 9 | 2-1 | 2-1 | HT2 | HOST1 | DOPANT1 | 1-5 | 7.2 | 4.1 | 69 |
| Example 10 | 2-1 | 2-1 | HT2 | HOST2 | DOPANT2 | 1-5 | 8.3 | 4.0 | 108 |
| Example 11 | 2-1 | 2-1 | HT2 | HOST1 | DOPANT1 | 1-8 | 6.7 | 3.9 | 72 |
| Example 12 | 2-1 | 2-1 | HT2 | HOST2 | DOPANT2 | 1-8 | 7.0 | 3.9 | 129 |

Referring to the results of Table 1, it could be found that the organic electroluminescence devices of the Examples using the first compound of an embodiment as a material for an electron transport layer showed excellent device efficiency properties. It can be found that the organic electroluminescence devices of Example 1 to Example 12 showed higher efficiency properties when compared with the organic electroluminescence devices of Comparative Example 1 to Comparative Example 4. Compound ET1 included in the electron transport layer of Comparative Example 3 and Comparative Example 4 includes a phenanthroline group, but the positions of the first compound of an embodiment and a substituent bonded to the phenanthroline group are different. In ET1 of Comparative Example 3 and Comparative Example 4, a substituent is bonded to carbon present at an ortho position to the nitrogen atom of the phenanthroline group. Differently, the first compound of an embodiment is different in that a substituent is bonded to carbon present at a meta or para position to the nitrogen atom of the phenanthroline group.

The organic electroluminescence devices of Comparative Example 1 and Comparative Example 3, and the organic electroluminescence devices of Examples 1, 3, 5, and 7 used the same materials for forming hole transport layers and emission layers. The organic electroluminescence devices of Examples 1, 3, 5, and 7 showed similar or lower level of a driving voltage and better device life characteristics when compared with those of the organic electroluminescence devices of Comparative Example 1 and Comparative Example 3. The organic electroluminescence devices of Comparative Example 1 and Comparative Example 3, and the organic electroluminescence devices of Example 9 and Example 11 included second hole transport layers and emission layers formed using the same materials. It could be found that the organic electroluminescence devices of Example 9 and Example 11 showed a reduced driving voltage and improved device life when compared with those of the organic electroluminescence devices of Comparative Example 1 and Comparative Example 3.

The organic electroluminescence devices of Examples 2, 4, 6, and 8, and the organic electroluminescence devices of Comparative Example 2 and Comparative Example 4 used the same materials for forming hole transport layers and emission layers. The organic electroluminescence devices of Examples 2, 4, 6, and 8 showed similar or lower level of a driving voltage and better device life characteristics when compared with those of the organic electroluminescence devices of Comparative Example 2 and Comparative Example 4. The same materials were used for forming second hole transport layers and emission layers of the organic electroluminescence devices of Example 10 and Example 12 as the materials of the organic electroluminescence devices of Comparative Example 2 and Comparative Example 4. It could be found that the organic electroluminescence devices of Example 10 and Example 12 showed similar or lower level of a driving voltage and better device life characteristics when compared with those of the organic electroluminescence devices of Comparative Example 2 and Comparative Example 4.

The first compound may contribute to the improvement of the moving speed of electrons, and the second compound may contribute to the improvement of the moving speed of holes. The organic electroluminescence device of an embodiment, including the first compound and the second compound increases the recombination probability of holes and electrons in an emission layer and is thought to show excellent emission efficiency characteristics when compared with those of the Comparative Examples.

The first compound of an embodiment, showing improved moving speed of electrons may be included in the organic electroluminescence device of an embodiment and may contribute to the decrease of a driving voltage and the improvement of emission efficiency.

The organic electroluminescence device of an embodiment includes the first compound in an electron transport region and a charge generating layer and may show a reduced driving voltage and excellent emission efficiency properties.

The organic electroluminescence device of an embodiment includes the compound of an embodiment in an electron transport region or a charge generating layer and may show improved device characteristics with high efficiency.

The compound of an embodiment is included in the electron transport region or charge generating layer of an organic electroluminescence device and may contribute to the improvement of the efficiency of the organic electroluminescence device.

Although the embodiments of the invention have been described, it is understood that the invention should not be limited to these embodiments but various changes and modifications can be made by one ordinary skilled in the art within the spirit and scope of the invention as hereinafter claimed.

What is claimed is:

1. An organic electroluminescence device, comprising:
a first electrode including at least one selected from the group consisting of Ag, Mg, Cu, Al, Pt, Pd, Au, Ni, Nd, Ir, Cr, Li, Ca, LiF/Ca, LiF/Al, Mo, Ti, In, Sn, Zn, oxides thereof, compounds thereof, and mixtures thereof;
a hole transport region disposed on the first electrode;
an emission layer disposed on the hole transport region;
an electron transport region disposed on the emission layer; and
a second electrode disposed on the electron transport region, wherein
the electron transport region comprises a first compound represented by Formula 1:

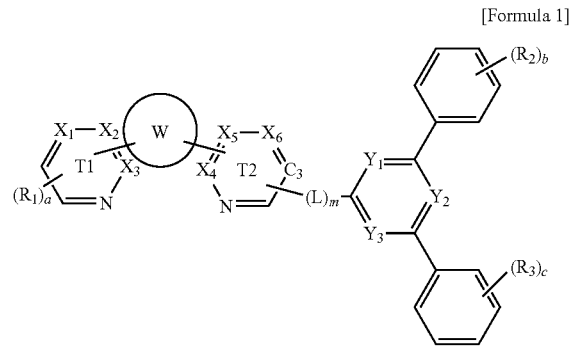

[Formula 1]

wherein in Formula 1,
$X_1$ to $X_6$ are each independently N or $CR_4$,
W is 0 or 1,
if W is 0, then $X_3$ and $X_4$ make a direct linkage,
if W is 1, then W is a substituted or unsubstituted hydrocarbon ring group of 4 to 60 ring-forming carbon atoms or a substituted or unsubstituted heterocyclic group of 1 to 60 ring-forming carbon atoms, and W is combined with ring T1 and ring T2 to form a polycyclic ring,
$C_3$ is C or CH,
m is an integer from 0 to 3,
L is a substituted or unsubstituted divalent hydrocarbon ring group of 4 to 60 ring-forming carbon atoms or a substituted or unsubstituted divalent heterocyclic group of 1 to 60 ring-forming carbon atoms,
if W, T1, and T2 are combined to form a phenanthroline group, then L is bonded to $C_3$,
at least one of $Y_1$ to $Y_3$ is N,
the remainder of $Y_1$ to $Y_3$ are each independently N or $CR_5$,
a is 1 or 2,
b and c are each independently an integer from 1 to 5,
$R_1$ to $R_5$ are each independently a hydrogen atom, a deuterium atom, a substituted or unsubstituted alkoxy group, a substituted or unsubstituted alkyl group of 1 to 60 carbon atoms, a substituted or unsubstituted alkenyl group of 2 to 60 carbon atoms, a substituted or unsubstituted alkynyl group of 2 to 60 carbon atoms, a substituted or unsubstituted aryl group of 6 to 60 ring-forming carbon atoms, a substituted or unsubstituted heteroaryl group of 1 to 60 ring-forming carbon atoms, or combined with an adjacent group to form a ring, and if $X_3$ and $X_4$ make a direct linkage, and $X_1$, $X_2$, $X_5$, and $X_6$ are all CH, then $R_1$ is not a hydrogen atom.

2. The organic electroluminescence device of claim 1, wherein Formula 1 is represented by one of Formula 1-1 to Formula 1-3:

[Formula 1-1]

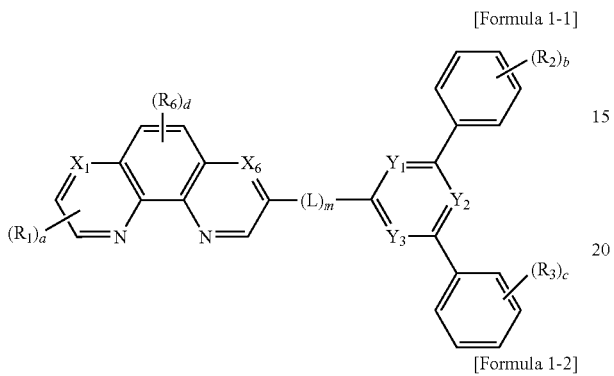

[Formula 1-2]

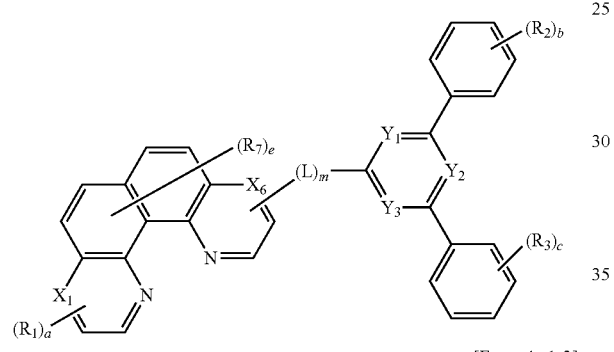

[Formula 1-3]

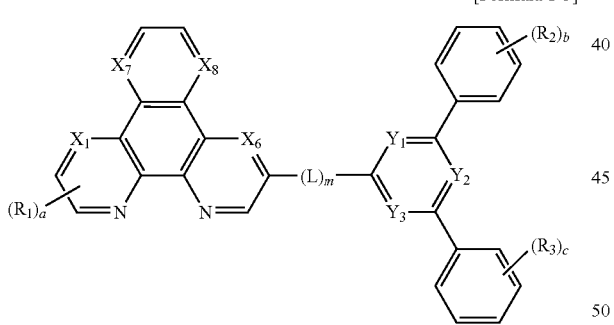

wherein in Formula 1-1, d is 1 or 2, wherein in Formula 1-2, e is an integer from 1 to 4, wherein in Formula 1-3, $X_7$ and $X_8$ are each independently N or $CR_8$, wherein in Formula 1-1 to Formula 1-3, $R_6$ to $R_8$ are each independently a hydrogen atom, a deuterium atom, a substituted or unsubstituted alkoxy group, a substituted or unsubstituted alkyl group of 1 to 60 carbon atoms, a substituted or unsubstituted alkenyl group of 2 to 60 carbon atoms, a substituted or unsubstituted alkynyl group of 2 to 60 carbon atoms, a substituted or unsubstituted aryl group of 6 to 60 ring-forming carbon atoms, or a substituted or unsubstituted heteroaryl group of 1 to 60 ring-forming carbon atoms, and a to c, L, m, $R_1$ to $R_3$, $X_1$, $X_6$, and $Y_1$ to $Y_3$ are the same as defined in Formula 1.

3. The organic electroluminescence device of claim 1, wherein Formula 1 is represented by Formula 1-4:

[Formula 1-4]

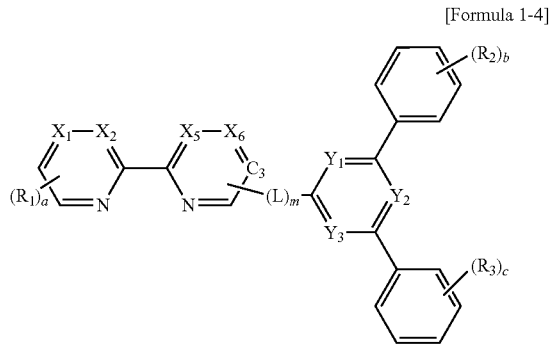

wherein in Formula 1-4, a to c, L, m, $R_1$ to $R_3$, $X_1$, $X_2$, $X_5$, $X_6$, $C_3$, and $Y_1$ to $Y_3$ are the same as defined in Formula 1.

4. The organic electroluminescence device of claim 1, wherein Formula 1 is represented by one of Formula 1-A to Formula 1-D:

[Formula 1-A]

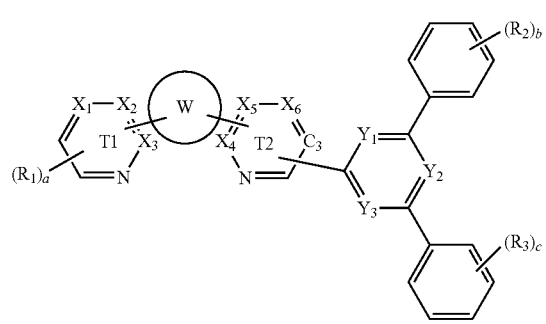

-continued

[Formula 1-B]

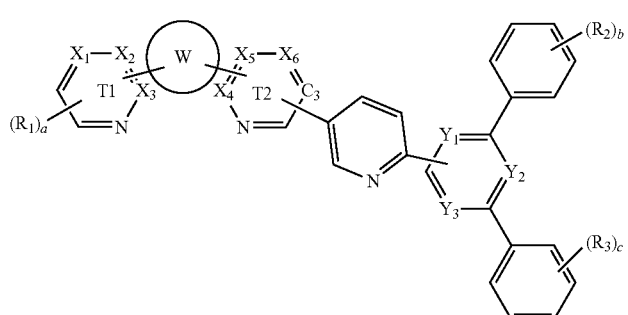

[Formula 1-C]

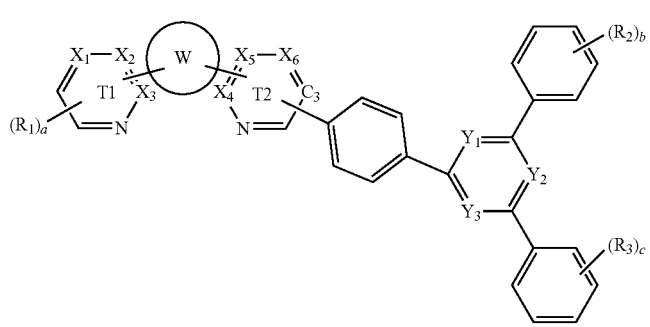

[Formula 1-D]

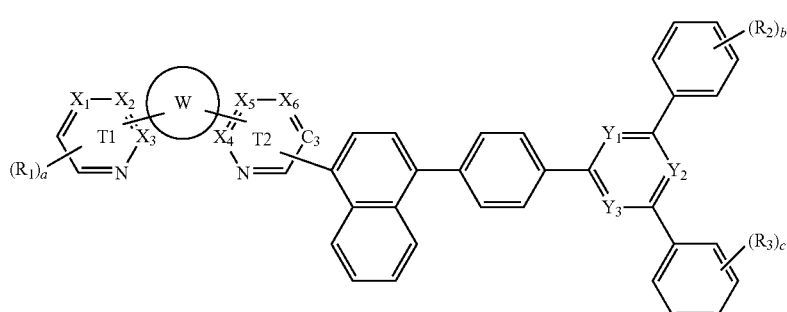

wherein in Formula 1-A to Formula 1-D, a to c, $R_1$ to $R_3$, W, T1, T2, $X_1$ to $X_6$, $C_3$, and $Y_1$ to $Y_3$ are the same as defined in Formula 1.

5. The organic electroluminescence device of claim 1, wherein $R_1$ is a group represented by one of $R_{1-1}$ to $R_{1-4}$:

$R_{1-1}$

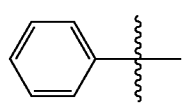

$R_{1-2}$ $R_{1-3}$

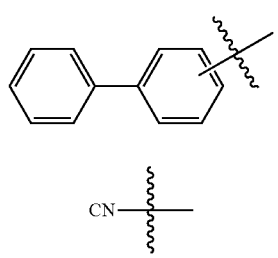

-continued $R_{1-4}$

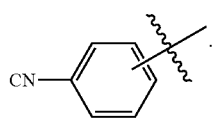

6. The organic electroluminescence device of claim 1, wherein the hole transport region comprises a second compound represented by Formula 2:

[Formula 2]

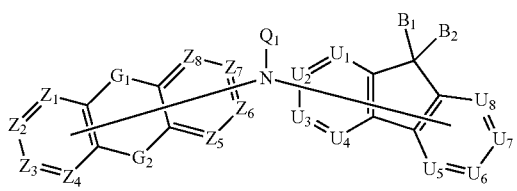

wherein in Formula 2,
Q$_1$ is a substituted or unsubstituted aryl group of 6 to 30 ring-forming carbon atoms or a substituted or unsubstituted heterocyclic group of 2 to 30 ring-forming carbon atoms,
G$_1$ is CR$_{11}$R$_{12}$, NR$_{13}$, O, or S,
G$_2$ is a direct linkage, CR$_{14}$R$_{15}$, SiR$_{16}$R$_{17}$, NR$_{18}$, O, S, or SO$_2$,
at least one of Z$_1$ to Z$_8$ is CR$_{19}$,
the remainder of Z$_1$ to Z$_8$ are each independently N or CR$_{19}$,
at least one of U$_1$ to U$_8$ is CR$_{20}$,
the remainder of U$_1$ to U$_8$ are each independently N or CR$_{20}$,
B$_1$ and B$_2$ are each independently a substituted or unsubstituted alkyl group of 1 to 20 carbon atoms, and
R$_{11}$ to R$_{20}$ are each independently a hydrogen atom, a deuterium atom, a halogen atom, an oxy group, a substituted or unsubstituted alkyl group of 1 to 60 carbon atoms, a substituted or unsubstituted alkenyl group of 2 to 60 carbon atoms, a substituted or unsubstituted alkynyl group of 2 to 60 carbon atoms, a substituted or unsubstituted aryl group of 6 to 60 ring-forming carbon atoms, or a substituted or unsubstituted heteroaryl group of 1 to 60 ring-forming carbon atoms.

7. The organic electroluminescence device of claim 6, wherein Formula 2 is represented by Formula 2-1:

[Formula 2-1]

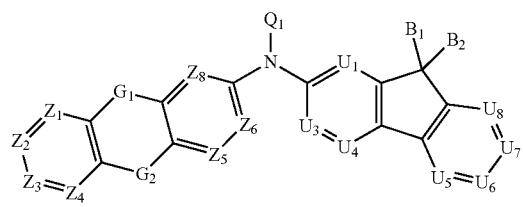

wherein in Formula 2-1,
Q$_1$, B$_1$, B$_2$, U$_1$, U$_3$ to U$_8$, G$_1$, G$_2$, Z$_1$ to Z$_6$, and Z$_8$ are the same as defined in Formula 2.

8. The organic electroluminescence device of claim 6, wherein Q$_1$ is a group represented by one of Q$_{1-1}$ to Q$_{1-5}$:

Q$_{1-1}$
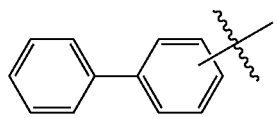

Q$_{1-2}$
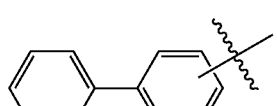

Q$_{1-3}$
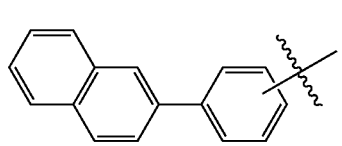

Q$_{1-4}$
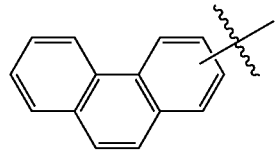

Q$_{1-5}$
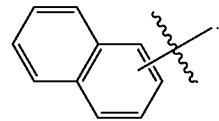

9. The organic electroluminescence device of claim 6, wherein
B$_1$ and B$_2$ are the same, and
B$_1$ and B$_2$ are unsubstituted alkyl groups of 2 to 10 carbon atoms.

10. The organic electroluminescence device of claim 6, wherein
the hole transport region comprises:
a hole injection layer;
a first hole transport layer disposed on the hole injection layer; and
a second hole transport layer disposed on the first hole transport layer,
at least one of the hole injection layer, the first hole transport layer, and the second hole transport layer comprises the second compound, and
at least one of the hole injection layer and the second hole transport layer comprises a p-dopant.

11. The organic electroluminescence device of claim 10, wherein the hole transport region further comprises:
an electron blocking layer disposed between the second hole transport layer and the emission layer.

12. The organic electroluminescence device of claim 1, wherein
the electron transport region comprises:
an electron transport layer; and
an electron injection layer disposed on the electron transport layer, and
at least one of the electron transport layer and the electron injection layer comprises the first compound.

13. The organic electroluminescence device of claim 12, wherein the electron transport region further comprises:
a hole blocking layer disposed between the emission layer and the electron transport layer.

14. The organic electroluminescence device of claim 1, wherein the first compound is one selected from Compound Group 1:

[Compound Group 1]

1-1
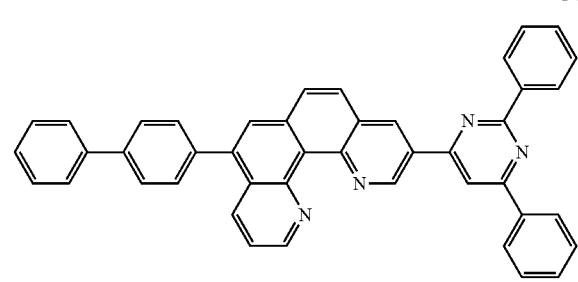

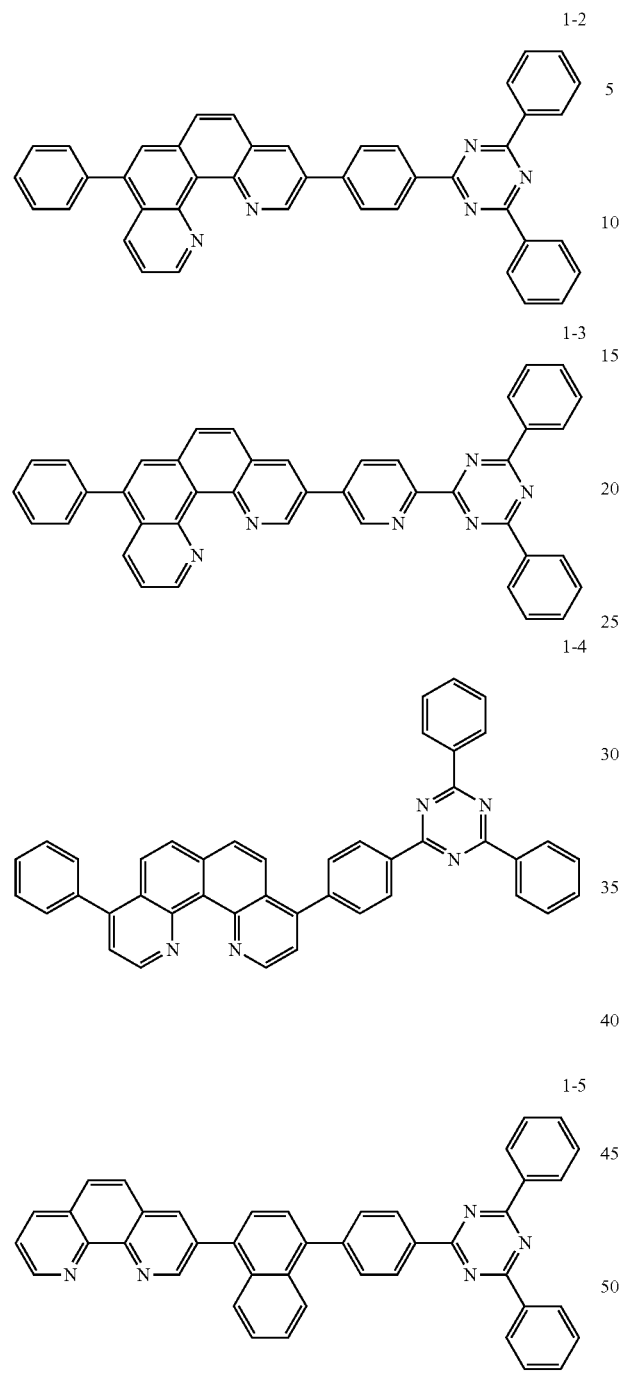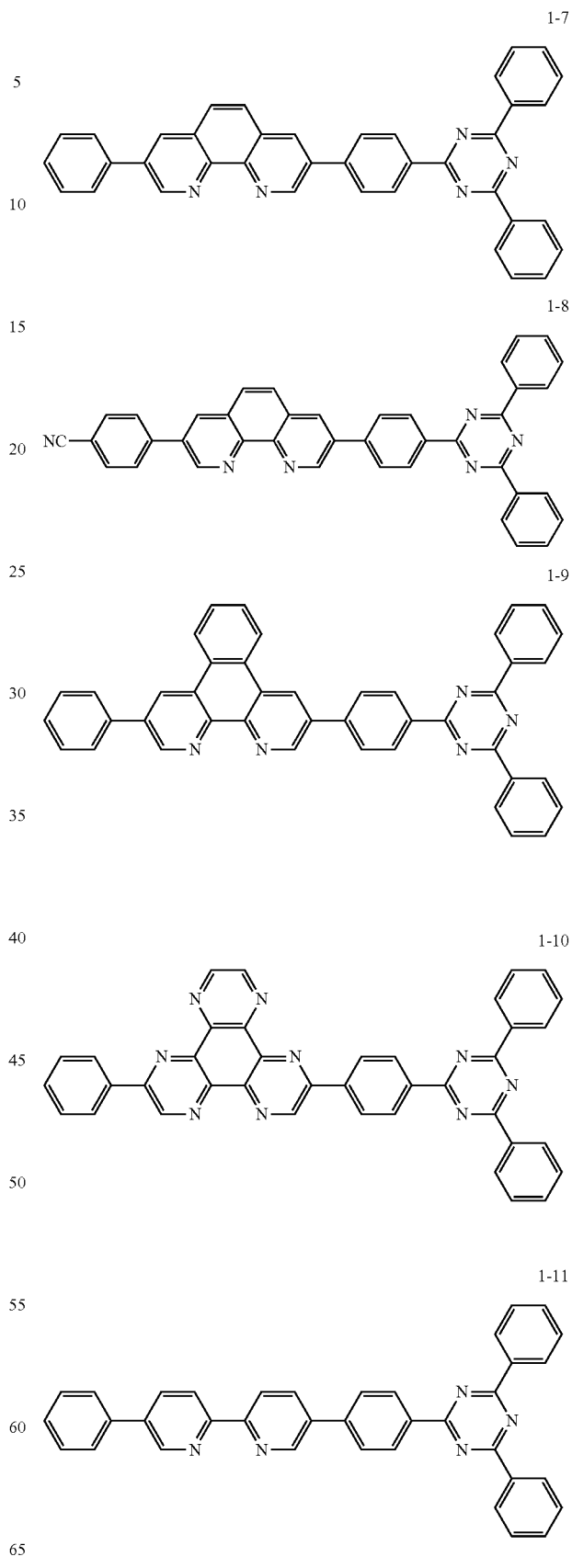

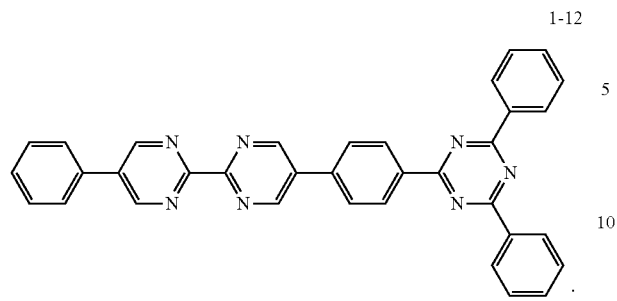
1-12
15. The organic electroluminescence device of claim 1, wherein the hole transport region comprises one selected from Compound Group 2:
[Compound Group 2]
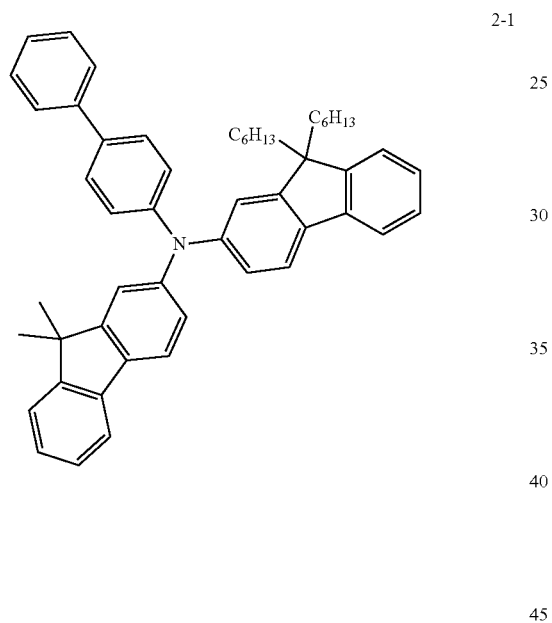
2-1
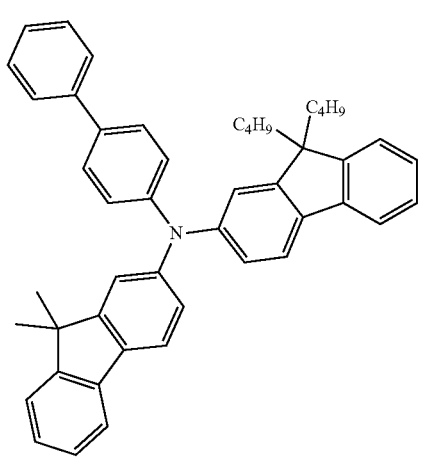
2-3
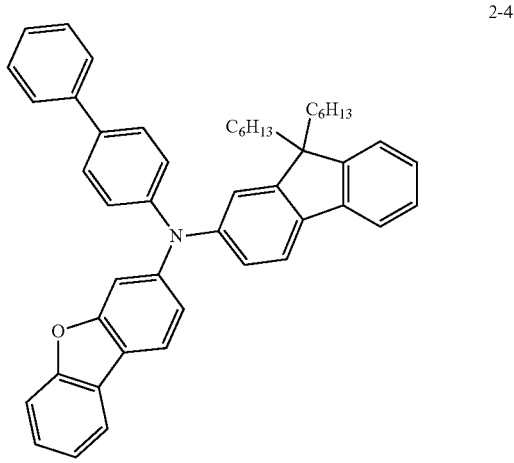
2-4
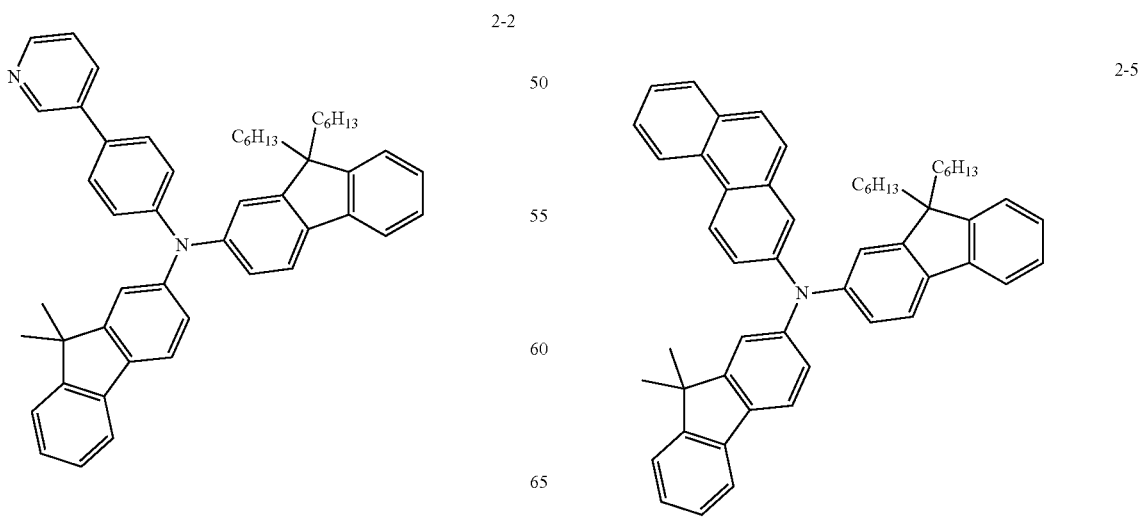

2-6

2-7

2-8

2-9

2-10

2-11

-continued

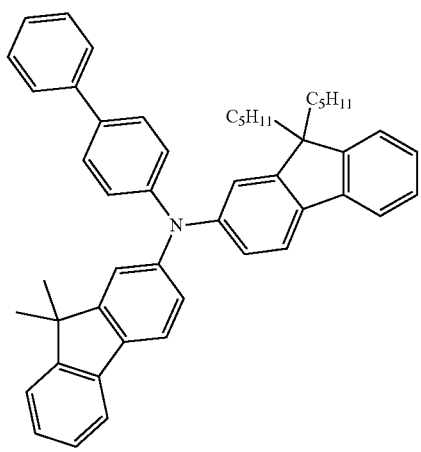
2-12

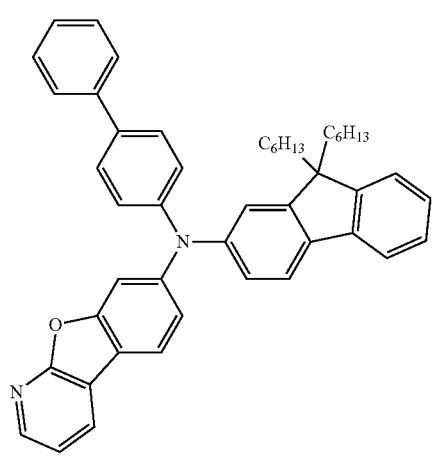
2-13

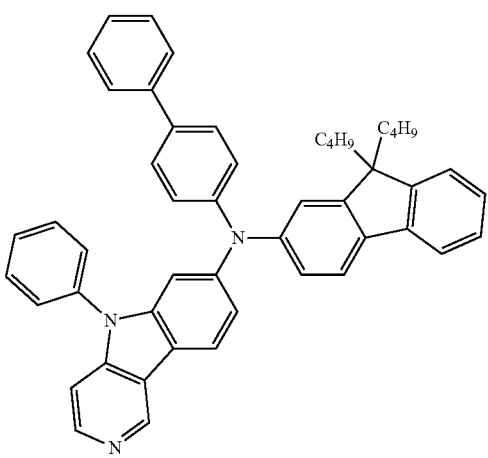
2-14

-continued

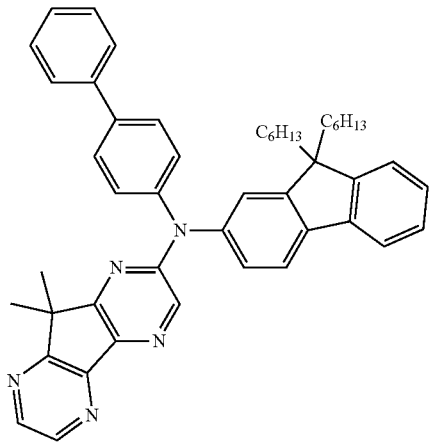
2-15

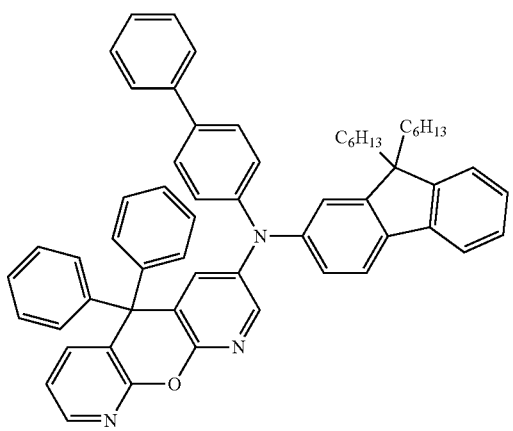
2-16

16. An organic electroluminescence device, comprising:
a first electrode including at least one selected from the group consisting of Ag, Mg, Cu, Al, Pt, Pd, Au, Ni, Nd, Ir, Cr, Li, Ca, LiF/Ca, LiF/Al, Mo, Ti, In, Sn, Zn, oxides thereof, compounds thereof, and mixtures thereof;
a second electrode disposed on the first electrode;
a plurality of light-emitting units disposed between the first electrode and the second electrode; and
at least one charge generating layer disposed between two adjacent ones of the plurality of light-emitting units, wherein
the at least one charge generating layer comprises a first compound represented by Formula 1:

[Formula 1]

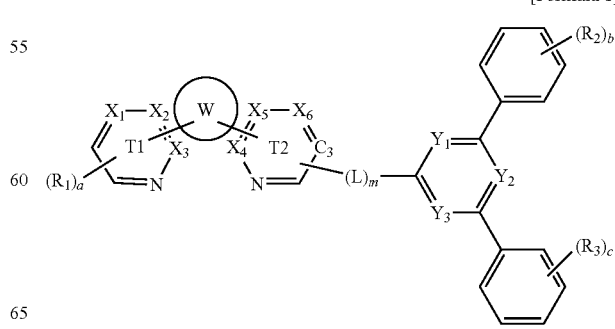

wherein in Formula 1, $X_1$ to $X_6$ are each independently N or $CR_4$,

W is 0 or 1, if W is 0, then $X_3$ and $X_4$ make a direct linkage, if W is 1, then W is a substituted or unsubstituted hydrocarbon ring group of 4 to 60 ring-forming carbon atoms or a substituted or unsubstituted heterocyclic group of 1 to 60 ring-forming carbon atoms, and W is combined with ring T1 and ring T2 to form a polycyclic ring, $C_3$ is C or CH, m is an integer from 0 to 3, L is a substituted or unsubstituted divalent hydrocarbon ring group of 4 to 60 ring-forming carbon atoms or a substituted or unsubstituted divalent heterocyclic group of 1 to 60 ring-forming carbon atoms, if W, T1, and T2 are combined to form a phenanthroline group, then L is bonded to $C_3$, at least one of $Y_1$ to $Y_3$ is N, the remainder of $Y_1$ to $Y_3$ are each independently N or $CR_5$, a is 1 or 2, b and c are each independently an integer from 1 to 5, $R_1$ to $R_5$ are each independently a hydrogen atom, a deuterium atom, a substituted or unsubstituted alkoxy group, a substituted or unsubstituted alkyl group of 1 to 60 carbon atoms, a substituted or unsubstituted alkenyl group of 2 to 60 carbon atoms, a substituted or unsubstituted alkynyl group of 2 to 60 carbon atoms, a substituted or unsubstituted aryl group of 6 to 60 ring-forming carbon atoms, a substituted or unsubstituted heteroaryl group of 1 to 60 ring-forming carbon atoms, or combined with an adjacent group to form a ring, and if $X_3$ and $X_4$ make a direct linkage, and $X_1$, $X_2$, $X_5$, and $X_6$ are all CH, then $R_1$ is not a hydrogen atom.

17. The organic electroluminescence device of claim 16, wherein the plurality of light-emitting units each comprise:

a hole transport region;

an emission layer disposed on the hole transport region; and an electron transport region disposed on the emission layer, the electron transport region comprises the first compound represented by Formula 1, and the hole transport region comprises a second compound represented by Formula 2:

[Formula 2]

wherein in formula 2, $Q_1$ is a substituted or unsubstituted aryl group of 6 to 30 ring-forming carbon atoms or a substituted or unsubstituted heterocyclic group of 2 to 30 ring-forming carbon atoms, $G_1$ is $CR_{11}R_{12}$, $NR_{13}$, O, or S, $G_2$ is a direct linkage, $CR_{14}R_{15}$, $SiR_{16}R_{17}$, $NR_{18}$, O, S, or $SO_2$, at least one of $Z_1$ to $Z_8$ is $CR_{19}$, the remainder of $Z_1$ to $Z_8$ are each independently N or $CR_{19}$, at least one of $U_1$ to $U_8$ is $CR_{20}$, the remainder of $U_1$ to $U_8$ are each independently N or $CR_{20}$, $B_1$ and $B_2$ are each independently a substituted or unsubstituted alkyl group of 1 to 20 carbon atoms, and $R_{11}$ to $R_{20}$ are each independently a hydrogen atom, a deuterium atom, a halogen atom, an oxy group, a substituted or unsubstituted alkyl group of 1 to 60 carbon atoms, a substituted or unsubstituted alkenyl group of 2 to 60 carbon atoms, a substituted or unsubstituted alkynyl group of 2 to 60 carbon atoms, a substituted or unsubstituted aryl group of 6 to 60 ring-forming carbon atoms, or a substituted or unsubstituted heteroaryl group of 1 to 60 ring-forming carbon atoms.

18. The organic electroluminescence device of claim 17, wherein the hole transport region comprises:

a hole injection layer;

a first hole transport layer disposed on the hole injection layer; and a second hole transport layer disposed on the first hole transport layer, at least one of the hole injection layer, the first hole transport layer, and the second hole transport layer comprises the second compound, and at least one of the hole injection layer and the second hole transport layer comprises a p-dopant.

19. The organic electroluminescence device of claim 17, wherein the electron transport region comprises:

an electron transport layer; and an electron injection layer disposed on the electron transport layer, and at least one of the electron transport layer and the electron injection layer comprises the first compound.

20. The organic electroluminescence device of claim 16, wherein the at least one charge generating layer comprises a compound selected from Compound Group 1:

[Compound Group 1]

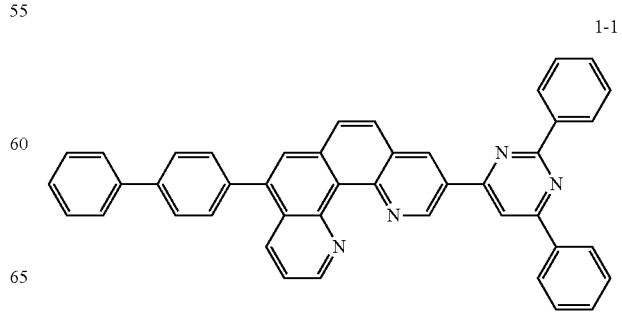

1-1

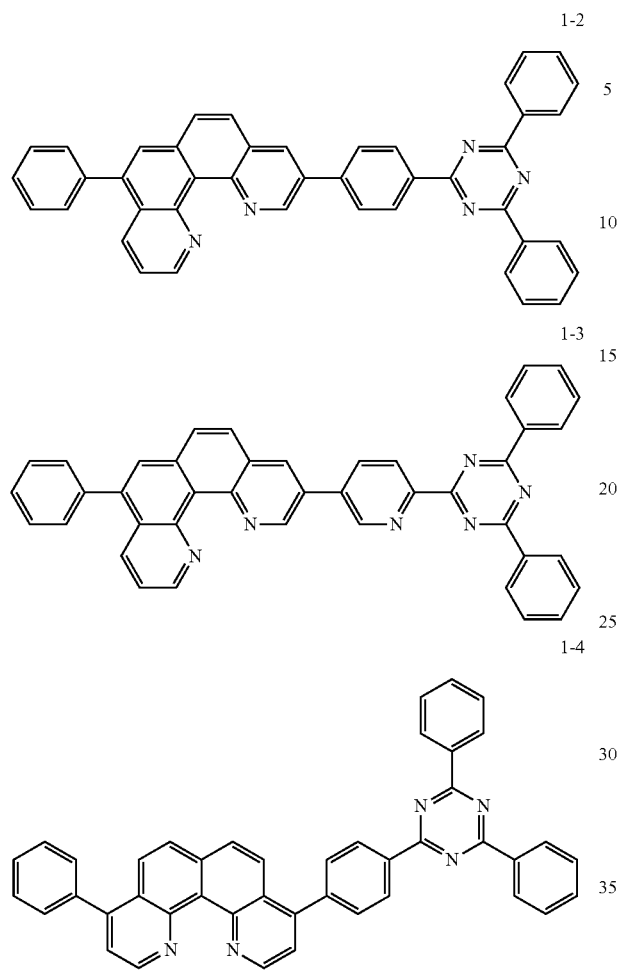
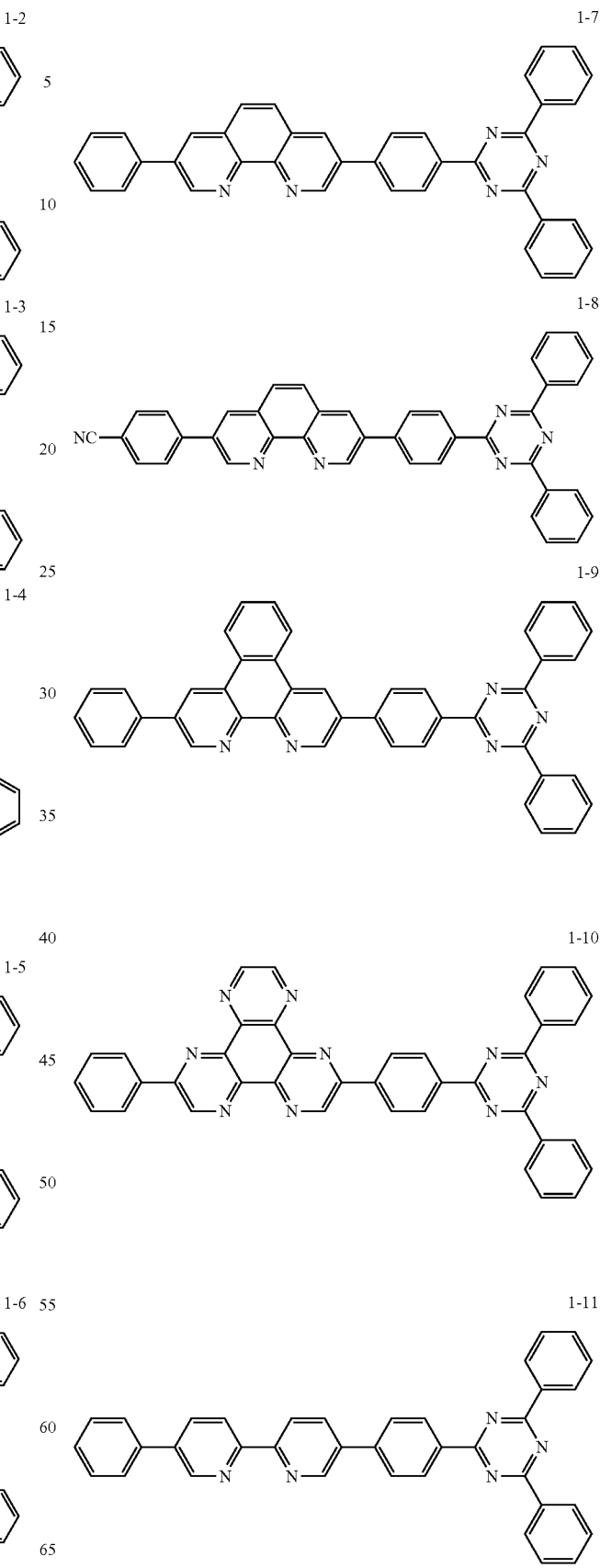

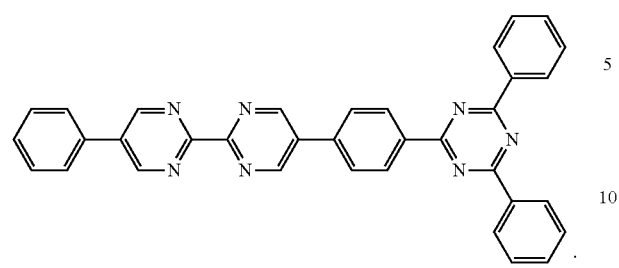
1-12
* * * * *

UNITED STATES PATENT AND TRADEMARK OFFICE
CERTIFICATE OF CORRECTION

| | | |
|---|---|---|
| PATENT NO. | : 12,324,351 B2 | Page 1 of 1 |
| APPLICATION NO. | : 18/495915 | |
| DATED | : June 3, 2025 | |
| INVENTOR(S) | : Hye Jeong Park et al. | |

It is certified that error appears in the above-identified patent and that said Letters Patent is hereby corrected as shown below:

In the Claims

In Column 65, Line 44, in Claim 7, delete "$Z_g$" and insert -- $Z_8$ --.

In Column 75, Line 62, in Claim 17, delete "formula" and insert -- Formula --.

Signed and Sealed this
Fourteenth Day of October, 2025

John A. Squires
*Director of the United States Patent and Trademark Office*